United States Patent
Kisak et al.

(10) Patent No.: US 12,070,440 B2
(45) Date of Patent: Aug. 27, 2024

(54) TOPICAL FORMULATIONS OF NITROGLYCERIN

(71) Applicant: PERMEATUS, INC., Del Mar, CA (US)

(72) Inventors: Edward T. Kisak, San Diego, CA (US); John M. Newsam, La Jolla, CA (US); R. Dominic King-Smith, Del Mar, CA (US)

(73) Assignee: PERMEATUS, INC., Del Mar, CA (US)

( * ) Notice: Subject to any disclaimer, the term of this patent is extended or adjusted under 35 U.S.C. 154(b) by 0 days.

(21) Appl. No.: 18/215,058

(22) Filed: Jun. 27, 2023

(65) Prior Publication Data

US 2023/0414551 A1    Dec. 28, 2023

Related U.S. Application Data

(60) Provisional application No. 63/356,024, filed on Jun. 27, 2022.

(51) Int. Cl.
| | | |
|---|---|---|
| *A61K 31/21* | (2006.01) | |
| *A61K 9/00* | (2006.01) | |
| *A61K 47/10* | (2017.01) | |
| *A61K 47/12* | (2006.01) | |
| *A61K 47/14* | (2017.01) | |
| *A61K 47/34* | (2017.01) | |
| *A61K 47/38* | (2006.01) | |
| *A61P 9/14* | (2006.01) | |

(52) U.S. Cl.
CPC .......... *A61K 31/21* (2013.01); *A61K 9/0014* (2013.01); *A61K 47/10* (2013.01); *A61K 47/12* (2013.01); *A61K 47/14* (2013.01); *A61K 47/34* (2013.01); *A61K 47/38* (2013.01); *A61P 9/14* (2018.01)

(58) Field of Classification Search
CPC ...... A61K 31/21; A61K 9/0014; A61K 47/10; A61K 47/12; A61K 47/14; A61K 47/34; A61K 47/38; A61P 9/14
See application file for complete search history.

(56) References Cited

U.S. PATENT DOCUMENTS

| 5,273,755 | A | * | 12/1993 | Venktrama | ............. | A61K 9/703 |
| | | | | | | 424/447 |
| 5,766,575 | A | * | 6/1998 | Crotty | .................... | A61K 8/347 |
| | | | | | | 424/47 |
| 2002/0049188 | A1 | * | 4/2002 | Azarnoff | ............. | A61K 9/0031 |
| | | | | | | 514/509 |
| 2004/0044080 | A1 | | 3/2004 | Place et al. | | |
| 2009/0028929 | A1 | * | 1/2009 | Stefanelli | ............... | A61K 31/21 |
| | | | | | | 514/506 |
| 2021/0069108 | A1 | * | 3/2021 | Weinberg | ........... | A61K 31/4422 |

FOREIGN PATENT DOCUMENTS

| EP | 0028526 B1 | 12/1980 |
| EP | 2878310 A1 | 6/2015 |
| WO | 9210154 A1 | 6/1992 |
| WO | 9532715 A1 | 12/1995 |

OTHER PUBLICATIONS

Product Sheet, "Ceraphyl 41 ester Effective de-tackifying agent and solubilizer," 2013 Ashland Ceraphyl-41-Datasheet.pdf (azeliscanada. com). (Year: 2013).*
International Search Report and Written Opinion for PCT/US2023/023380, dated Oct. 17, 2023, 10 pages.

* cited by examiner

*Primary Examiner* — Jared Barsky

(74) *Attorney, Agent, or Firm* — PROCOPIO, CORY, HARGREAVES & SAVITCH LLP

(57) ABSTRACT

The present disclosure relates generally to compositions of nitroglycerin and related organic nitrates, and methods for treating conditions such as Raynaud's phenomenon in which peripheral blood flow in a subject is compromised.

17 Claims, 5 Drawing Sheets

TOPICAL FORMULATIONS OF NITROGLYCERIN

BACKGROUND OF THE DISCLOSURE

Nitroglycerin, also known as nitroglycerine, trinitroglycerin, nitro, glyceryl trinitrate (GTN), or 1,2,3-trinitroxypropane, has been used for over 130 years in medicine as a potent vasodilator to treat heart conditions, such as angina pectoris and chronic heart failure. The beneficial effects arise from conversion of nitroglycerin by mitochondrial aldehyde dehydrogenase (mtALDH2) to nitric oxide (NO), a potent venodilator.

Outside the body, nitroglycerin (GTN) decomposes by denitration to 1,2-glyceryl dinitrate (1,2-GDN) with formation of nitrate ions ($NO^{3-}$). The decomposition is slow at pH 7.4, but faster in an acidic environment (0.1N HCl), and rapid at pH values of 11 and above. 1,2-GDN interconverts to 1,3-dinitroglycerin (1,3-GDN) and both 1,2-GDN and 1,3-GDN degrade further, again with formation of nitrate ions, to 1-mononitroglycerin (1-MNG) or 2-mononitroglycerin (2-MNG).

In contrast, GTN biotransformation is tissue and cell specific, and dose dependent, and it yields 1,2-GDN, 1,3-GDN, inorganic nitrite, and NO (or S-nitrosothiol (SNO)) in differing amounts and ratios. In vascular smooth muscle cells, mitochondrial aldehyde dehydrogenase (mtALDH) reduces GTN specifically to 1,2-GDN. Vasorelaxation-related formation of 1,2-GDN is diminished in GTN-tolerant blood vessels as a result of compromised mtALDH activity. The nitrite ions ($NO_2^-$) are reduced to NO by cytochrome be 1 complex (complex III) and cytochrome c oxidase (complex IV) in the mitochondrial electron transport chain. Nitrite might also be transported into the intermembrane space where the higher proton concentration may facilitate its conversion to NO (or SNO).

SUMMARY OF THE DISCLOSURE

One aspect of the present disclosure provides topical formulations of nitroglycerin and methods for treating conditions in which peripheral blood flow in a subject is compromised.

In some embodiments, there is provided herein a pharmaceutically-acceptable topical composition comprising nitroglycerin that is essentially free of both water and hydrocarbon.

In some embodiments, there is provided herein a pharmaceutically-acceptable topical composition comprising at least 4% weight by weight of nitroglycerin that is essentially free of both water and hydrocarbon.

In some embodiments, there is provided herein a pharmaceutically-acceptable topical composition comprising at least 4% weight by weight of nitroglycerin and further comprising at least 50% weight by weight of propylene glycol.

In some embodiments, there is provided herein a pharmaceutically-acceptable topical composition that is essentially free of water and hydrocarbon and which comprises at least 5% weight by weight of nitroglycerin, and at least 50% weight by weight of propylene glycol.

In some embodiments, there is provided a topical composition of the disclosure further comprising a viscosity-modifying agent selected from hydroxypropyl cellulose, polyoxyethylene sorbitan monooleate, acrylamide/sodium acryloyldimethyl taurate copolymer, SEPINEO P600, or a mixture thereof.

In some embodiments, there is provided herein a topical composition of the disclosure further comprising a fatty acid.

In some embodiments, there is provided herein a topical composition of the disclosure wherein said fatty acid is oleic acid or isostearic acid.

In some embodiments, there is provided herein a topical composition of the disclosure further comprising an emollient.

In some embodiments, there is provided herein a topical composition of the disclosure wherein said emollient comprises a fatty acid ester of an alpha hydroxy acid.

In some embodiments, there is provided herein a topical composition of the disclosure wherein said fatty acid ester of an alpha hydroxy acid comprises a C12, C13, C14 or C15 alkyl ester of lactic acid, Ceraphyl 41, or a mixture thereof.

In some embodiments, there is provided herein a topical composition of the disclosure further comprising a lubricity-enhancing agent.

In some embodiments, there is provided herein a topical composition of the disclosure wherein said lubricity-enhancing agent is a silicone.

In some embodiments, there is provided herein a pharmaceutically-acceptable topical composition that is essentially free of water and hydrocarbon comprising at least 7% weight by weight of nitroglycerin, at least 70% weight by weight of propylene glycol, at least 8% oleic acid, about 1.5% Ceraphyl 41 and about 3% of hydroxypropyl cellulose.

In some embodiments, there is provided herein a pharmaceutically-acceptable topical composition comprising at least 3% weight by weight of nitroglycerin that is essentially free of water, hydrocarbon and ethanol.

In some embodiments, there is provided herein a pharmaceutically-acceptable topical composition that is essentially free of water and hydrocarbon comprising at least 3% weight by weight of nitroglycerin and in which nitroglycerin degrades by less than 5% when stored at 25° C. for at least six months.

In some embodiments, there is provided herein a topical composition of the disclosure further comprising an agent which indicates to which area of skin said topical composition has been applied.

In some embodiments, there is provided herein a topical composition of the disclosure which said agent comprises a colorant.

In some embodiments, there is provided a pharmaceutically-acceptable topical composition comprising:
 (i) about 0.5 to 10% w/w of an active agent;
 (ii) at least about 50% w/w of a diluent;
 (iii) about 1 to 15% w/w of a fatty acid;
 (iv) optionally about 0.5 to 5% w/w of an emollient;
 (v) about 0.1 to 5% w/w a lubricity-enhancing agent;
 (vi) about 0.5 to 10% w/w viscosity-modifying agent;
 (vii) optionally about 0.25 to 15% w/w of an MPE; and
 (viii) optionally an antioxidant.

In some embodiments, there is provided a pharmaceutically-acceptable topical composition of the above wherein:
 (i) the active agent is selected from nitroglycerin (GTN), trinitroglycerin, nitro, glyceryl trinitrate, 1,2,3-trinitroxypropane pentaerythritol tetranitrate (PETN), isosorbide dinitrate (ISDN), isosorbide mononitrate (ISMN), or 1,2-dialkoxy-2-propyl nitrates;
 (ii) the diluent is selected from alcohols, medium chain triglycerides, Miglyol 812, a mixture of caprylic triglyceride and capric triglyceride, or propylene glycol;
 (iii) the fatty acid is selected from oleic acid or isostearic acid;

(iv) the emollient is selected from a fatty acid ester of an alpha hydroxy acid comprising a C12, C13, C14 or C15 alkyl ester of lactic acid;
(v) the lubricity-enhancing agent is selected from a silicone or cyclic siloxane;
(vi) the viscosity-modifying agent is selected from hydroxypropyl cellulose, polyoxyethylene sorbitan monooleate, acrylamide/sodium acryloyldimethyl taurate copolymer or a mixture thereof,
(ix) the MPE is selected from Brij L4, isopropyl myristate, isopropyl palmitate, dimethyl isosorbide, di(ethylene glycol) ethyl ether or a mixture thereof; and
(x) the antioxidant comprises butylated hydroxytoluene (BHT).

In some embodiments, there is provided a pharmaceutically-acceptable topical composition comprising:
(i) about 0.5 to 10% w/w nitroglycerin;
(ii) at least 50% w/w propylene glycol;
(iii) about 1 to 15% w/w oleic acid or isostearic acid;
(iv) optionally about 0.5 to 50% w/w Ceraphyl 41;
(v) about 0.1 to 5% w/w cyclomethicone;
(vi) about 0.5 to 10% w/w hydroxypropyl cellulose or SEPINEO P 600; and
(vii) optionally about 0.25 to 15% w/w Brij L4, isopropyl myristate, dimethyl isosorbide, di(ethylene glycol) ethyl ether or a mixture thereof, and
(viii) optionally about 0.05 to 0.8% w/w butylated hydroxytoluene (BHT).

In some embodiments, there is provided herein a method for treating a condition in a subject in which peripheral blood flow is compromised comprising topical administration of a formulation composition of the disclosure.

In some embodiments, there is provided herein a method of the disclosure wherein said condition is a chronic tendinopathy, mastectomy skin flap necrosis, autonomic dysreflexia associated with spinal cord injury, intraoperative microsurgical vasospasm, radial artery vasodilation prior to cannulation, chondrodermatitis nodularis helicis, chronic anal fissure, introital dyspareunia, vulvar pain associated with vulvodynia, or Raynaud's phenomenon.

In some embodiments, there is provided herein a method of the disclosure wherein said condition is selected from the group consisting of peripheral artery disease, peripheral vascular disease, diabetic neuropathy, tendinopathy, erectile dysfunction, alopecia, male pattern baldness and female pattern baldness.

In some embodiments, there is provided herein a method of the disclosure wherein said condition is associated with secondary Raynaud's phenomenon connected with one or more of: systemic sclerosis, CREST syndrome, systemic lupus erythematosus, rheumatoid disease, rheumatoid arthritis, Sjogren's syndrome, or polymyositis.

In some embodiments there is provided herein a method of the disclosure wherein said condition is primary Raynaud's phenomenon.

In some embodiments, there is provided herein a method for ameliorating a symptom associated with compromised peripheral blood flow in a subject comprising topical administration of a formulation composition of the disclosure.

In some embodiments, there is provided herein a method of the disclosure wherein said symptom comprises skin redness, cyanosis of the skin, skin blanching, low skin temperature, pain in the hands or feet, numbness in the hands or feet, tingling in the hands or feet, parasthesia, throbbing in the hands or feet, and the number of Raynaud's attacks in the hands or feet.

In some embodiments, there is provided herein a method of the disclosure wherein said subject has a likelihood or severity of headache that is reduced relative to that which accompanies application to the skin of said subject of 2% nitroglycerin ointment USP according to the label directions for the treatment of angina pectoris.

In some embodiments, there is provided herein a method for treating or ameliorating Raynaud's phenomenon in a subject comprising application to the skin of the fingers of said subject a pharmaceutically acceptable topical formulation of nitroglycerin that is essentially free of both water and hydrocarbon wherein the viscosity of said formulation is less than 10,000 centipoise.

In some embodiments, there is provided herein a method of the disclosure wherein said topical formulation of nitroglycerin is applied to the subject at a dose per unit area of skin of no more than about 10 mg cm$^{-2}$ or no more than about 5 mg cm$^{-2}$.

In some embodiments, there is provided herein a method of the disclosure wherein no more than about 200 µL of said topical formulation of nitroglycerin is applied to a hand or digits of the subject.

In some embodiments, there is provided herein a method of the disclosure wherein said topical formulation of nitroglycerin is applied to the subject once per day, twice per day, thrice per day or on an as needed basis.

In some embodiments, there is provided herein a method of the disclosure wherein said topical formulation of nitroglycerin is applied once per day in the morning.

In some embodiments, there is provided herein a method of the disclosure wherein the last application of said topical formulation of nitroglycerin in a day is at least two, three, four, five or six hours before the subject's bedtime.

In some embodiments, there is provided herein a method of the disclosure, wherein the timing of said administration is indicated to said subject by a device worn by said subject.

In some embodiments, there is provided herein a method of the disclosure wherein said topical formulation of nitroglycerin provides no warming sensation when applied to the skin of said subject.

In some embodiments, there is provided herein a method of the disclosure wherein said topical formulation of nitroglycerin provides no cooling sensation when applied to the skin of said subject.

In some embodiments, there is provided herein a method of the disclosure wherein said treatment or amelioration is evidenced in a randomized placebo-controlled clinical study.

In some embodiments, there is provided herein a method of the disclosure wherein said treatment or amelioration is realized without a requirement for one or more of: (i) said formulation coming into contact with the skin of the other hand; (ii) rubbing said formulation into the skin; (iii) spreading said formulation by other than the container in which said topical formulation is provided.

In some embodiments, there is provided herein a method of the disclosure wherein said subject evidences in a controlled study an ability to hold the hand to which said topical formulation of nitroglycerin is applied in ice water for a period that is at least 50% longer after said administration than prior to said administration.

In some embodiments, there is provided herein a method of treating a subject suffering from Raynaud's phenomenon comprising provision to said subject of a composition of the disclosure together with instructions advising that the amount of said topical formulation of nitroglycerin applied to a hand or digits is to be adjusted based on the size of the hand or digits.

In some embodiments, there is provided herein a method of treating a subject suffering from Raynaud's phenomenon comprising provision to said subject of a composition of the disclosure together with instructions advising that said topical formulation of nitroglycerin is not to be transported by air.

In some embodiments, there is provided herein a kit for provision to a subject suffering from Raynaud's phenomenon comprising a composition of the disclosure together with instructions as to how much of said topical formulation of nitroglycerin is to be administered according to the hand size of said subject.

In some embodiments, there is provided herein a method of the disclosure wherein when said formulation composition is applied to a hand of said subject and said subject handwrites on paper with said hand in an uncovered state within 20 minutes of said topical administration, no transference of remnant topical formulation is visible on said paper.

In some embodiments, there is provided herein a method of the disclosure wherein a single instance of said topical administration results in a peak concentration of nitroglycerin in the blood plasma of said subject no greater than realized following administration of 2% ointment according to the label directions.

In some embodiments, there is provided herein a method of the disclosure wherein a single instance of said topical administration results in a peak concentration of 1,2 glycerol dinitrate in the blood plasma of said subject in the range of 0.4 ng/mL to 2.0 ng/mL.

In some embodiments, there is provided herein a method of the disclosure wherein a single instance of said topical administration results in a peak concentration of 1,3 glycerol dinitrate in the blood plasma of said subject in the range of 0.4 ng/mL to 2.0 ng/mL.

In some embodiments, there is provided herein a method for treating equine laminitis in an equine subject comprising topical administration of a formulation composition of the disclosure.

BRIEF DESCRIPTION OF THE DRAWINGS

A better understanding of the features and advantages of the present disclosure will be obtained by reference to the following illustrative embodiments, in which the principles of the disclosure are utilized, and the accompanying drawings of which.

DETAILED DESCRIPTION OF THE DISCLOSURE

Figure 1:
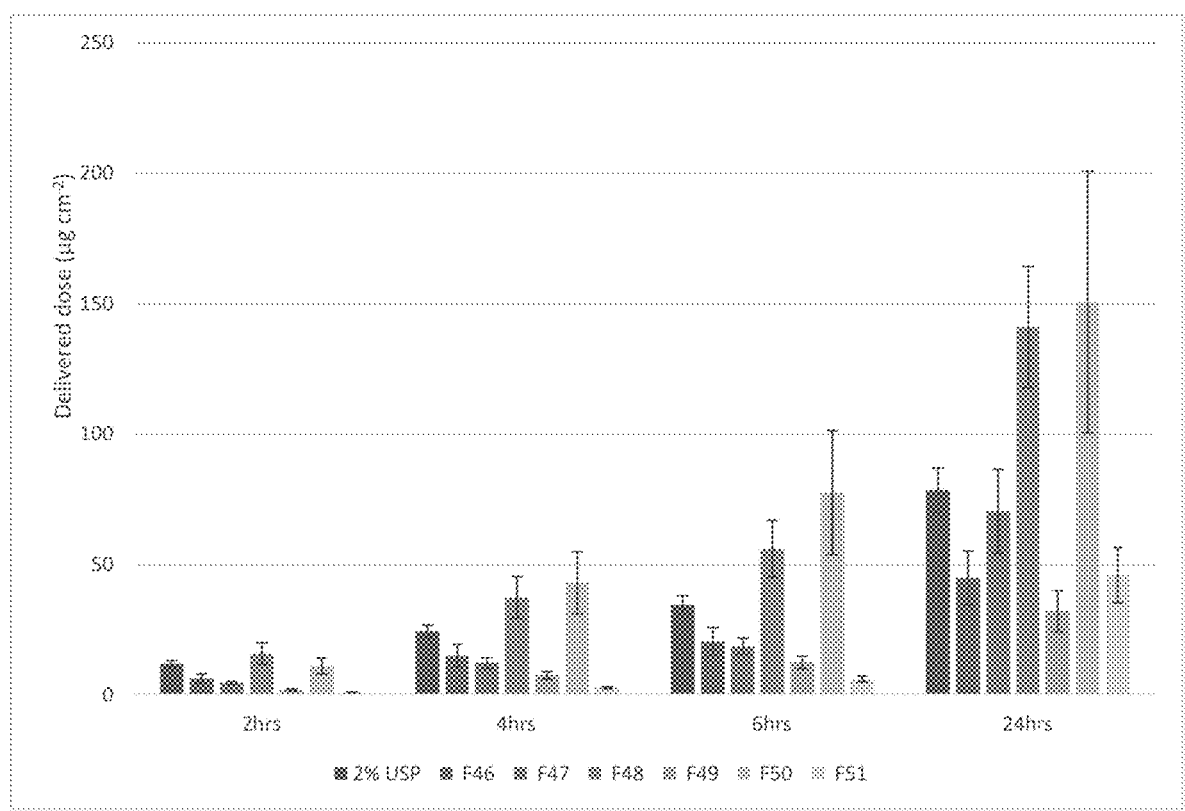
FIG. 1 illustrates the amounts of GTN, combined with its degradants, that have permeated through split-thickness human cadaver skin at 2, 4, 6 and 24 hours following application of each of the topical GTN formulations detailed in Table 5, as described in Example 4 provided herein.

The present disclosure recognizes that, it is desirable to have an efficacious topical medication that is safe when administered to the patient and safe during manufacturing, e.g. safe for employees involved in chemistry, manufacturing and control ("CMC") work. Nitroglycerin is an explosive liquid. Alfred Nobel developed ways to handle GTN only after his younger brother had been killed in an explosion. Dynamite comprises between 20% and 60% nitroglycerin. For pharmaceutical preparations, GTN is provided as a solution in an appropriate diluent, typically in a ratio of nitroglycerin to solvent of 1:10 (so 10% nitroglycerin, half of the amount in dynamite at its lower end) or greater.

The present disclosure recognizes that solutions in propylene glycol (10% w/w of GTN) and ethanol (5%) are available from Copperhead Chemical Company Inc. (Tamaqua, PA), in unspecified solvents from Cambrex Corporation (East Rutherford, NJ) and Valsynthese SA (Brig, Switzerland), in ethanol (5% & 1%), propylene glycol (10%) and Miglyol 812 (5%) from Novasep Holding SAS (Lyon, France), in ethanol (5%), propylene glycol (5%) and Miglyol (5%, 0.4% & 0.35%) from Dorsa Pharmaceutical (Tehran, Iran) (Miglyol is a mix of medium chain triglycerides).

The present disclosure recognizes that the presence of a diluent has greatly limited the range of practical GTN topical formulations, as compositions that provide suitable chemical and physical stability, release, skin permeation, and esthetic characteristics have proven elusive.

The present disclosure recognizes that not only is nitroglycerin explosive, but it is also susceptible to chemical degradation, especially in the presence of water under basic and acidic conditions. To be practicable for therapeutic use, it is desirable for a pharmaceutical preparation to have chemical and physical stability under the conditions of shipment and storage over a reasonable shelf-life period. Typically, a topical drug product is expected to be stable for two years under normal storage conditions. It is particularly desirable that a pharmaceutical composition maintain greater than 90% of its nominal potency for two years at 25° C.

The present disclosure recognizes that the diluent with which the GTN is combined, for safety reasons, is necessarily incorporated into the topical composition and at a typical concentration of 10 to 100 times that of GTN. It has not proven possible to overcome the difficulties involved in engineering a practicable topical formulation at a high GTN strength with the attendant high level of diluent. Further, no formulation of an organic nitrate in a topical solution or gel formulation which is comprised of more than 60% of a single excipient is yet available to patients.

The present disclosure recognizes that practicable topical formulations that comprise GTN are useful in the treatment of peripheral blood flow diseases, disorders of conditions, including Raynaud's phenomenon.

Disclosed herein are embodiments of formulations that are exceptionally effective at delivering nitroglycerin rapidly into the skin of a subject, and methods of treating conditions such as Raynaud's phenomenon in which peripheral blood flow is compromised by topical administration of such formulations.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Definitions

Unless defined otherwise, technical and scientific terms used herein have the same meaning as commonly understood by one of ordinary skill in the art to which the present disclosure belongs. For purposes of the present disclosure, the following terms are defined below.

The terms "a", "an", or "the" as used herein not only include aspects with one member, but also include aspects with more than one member. For example, an embodiment including "a cellulosic thickening agent and a lower monohydric alcohol" is to be understood to present certain aspects with at least a second cellulosic thickening agent, at least a second lower monohydric alcohol, or both. An embodiment including "an active agent" is to be understood to present certain aspects with at least a second active agent, which may be of a different class (e.g., lidocaine with a non-steroidal anti-inflammatory drug, or with an anti-inflammatory steroid, or with a local anesthetic, or with a sunscreen agent).

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X". When the quantity "X" only includes whole-integer values (e.g., "X carbons"), "about X" indicates from (X−1) to (X+1). In this case, "about X" as used herein specifically indicates at least the values X, X−1, and X+1. When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%."

The term "antimicrobial" or "preservative" refers to a substance that destroys microbes, such as a bactericide, or which prevents the propagation of microbes, such as a bacteriostatic compound.

The term "antioxidant" refers to a substance that inhibits oxidation.

Throughout this specification, unless the context requires otherwise, the words "comprise," "comprises," and "comprising" is open ended language and will be understood to imply the inclusion of a stated step or element or group of steps or elements but not the exclusion of any other step or element or group of steps or elements.

By "consisting of" is meant limited to, whatever follows the phrase "consisting of" Thus, the phrase "consisting of" is close ended and indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In compositions comprising an "additional" or "second" component, the second component, unless otherwise indicated, as used herein is chemically different from the other components or first component. A "third" component, unless otherwise indicated, is different from the other, first, and second components, and further enumerated or "additional" components are similarly different.

"Agent" as used herein indicates a compound or mixture of compounds that, when added to a composition, tend to produce a particular effect on the said composition's properties or performance. For example, a composition comprising a thickening agent is likely to be more viscous than an otherwise identical comparative composition that lacks the thickening agent; a composition comprising an active agent is more likely to provide a beneficial effect in the subject to which the composition is administered that otherwise.

As used herein, the term "bioavailability" has its ordinary meaning as understood in light of the specification and refers to the measure of the percentage of applied active pharmaceutical ingredient that becomes available to the target tissue. For an active pharmaceutical ingredient that has systemic benefit, bioavailability refers to the percentage of the applied dose that reaches the systemic circulation (from which it is available to the intended site of action); intravenous administration results in a bioavailability of 100%. For a drug product intended to provide topical delivery, cutaneous bioavailability refers to the percentage of the applied dose that is provided to the viable skin compartments.

The term "buffer" refers to either a weak acid or weak base, such that upon addition to an aqueous solution, a buffer solution is formed, which only slightly changes its pH in response to other acids and bases being combined with it, particularly a strong acid or a strong base. A buffer solution (more precisely, pH buffer or hydrogen ion buffer) refers to an aqueous solution consisting of a mixture of a weak acid and its conjugate base, or vice-versa. Its pH changes little when a small amount of strong acid or base is added to it. Buffer solutions are used as a means of maintaining pH at a nearly constant value.

"Carbon atom number" or "C" is used in its conventional sense to mean the number of carbon atoms in an organic compound such as a fatty alcohol or fatty acid. Thus, stearyl alcohol (1-octadecanol), isostearyl alcohol (1-Heptadecanol, 16-methyl-), and oleyl alcohol (1-octadecenol) might each be referred to as C18 fatty alcohols; cetyl alcohol (1-hexadecanol) and palmitoleyl alcohol (cis-9-hexadecen-1-ol) might both be referred to as C16 fatty alcohols; lauric acid, myristic acid, palmitic acid and stearic acid might be referred to as a C12, a C14, a C16 and C18 fatty acid, respectively. In the conventional designation of fatty acids and fatty alcohols, the number of double bonds in the carbon chain is also provided. Thus, oleic acid with a single carbon-carbon double bond is designated by (C18:1), and arachidonic acid with four carbon-carbon double bonds is designated by (C20:4).

The terms "chassis", "vehicle" and "base formulation" as used interchangeably herein are equivalent terms that include a one or more solvents or other excipients that comprise the bulk of a formulation, into which one or more active agents or additional agents might be introduced.

As used herein the term "comparative formulation" as it relates to a first formulation containing an active ingredient refers to a second formulation containing the same active ingredient. Generally, for the second formulation to qualify as a comparative formulation the concentration of the active ingredients is to be approximately the same in the first and second formulation.

The terms "composition" and "formulation" as used interchangeably herein refer to a material or mixture produced from a plurality of ingredients that are combined physically or chemically according to a formula or recipe.

The term "cyclomethicone" refers to a group of methyl siloxanes, a class of liquid silicones (cyclic polydimethylsiloxane polymers) that possess the characteristics of low viscosity and high volatility.

As used herein, the term "diluent" means a fluid in which GTN is soluble and in which GTN has reasonable chemical stability, but which is otherwise suitable for incorporation into a pharmaceutical formulation.

As used herein, the term "dosage form" has its ordinary meaning as understood in light of the specification and refers to the format of the material by which the active pharmaceutical ingredient and any excipients are provided to a subject. Dosage forms suitable for topical administration include solutions, viscous solutions, gels, lotions, creams, ointments, liniments, balms, aerosol sprays, foams, films, patches and pastes.

As used herein, the phrase "effective amount" or "effective dose" means an amount sufficient to achieve the desired result and accordingly will depend on the ingredient and its desired result. Nonetheless, once the desired effect is known, determining the effective amount is within the skill of a person skilled in the art. Effective amount includes an amount of topical formulation effective for treating or preventing a disease in a subject as described herein.

As used herein, the terms "efficacy", "intrinsic activity", and "potency" have their ordinary meaning as understood in light of the specification and refers to the amount of active pharmaceutical ingredient that is needed to achieve a desired effect. Efficacy or potency can be quantified as the median or 50% effective dose ($ED_{50}$), the dose that imparts a specific effect in 50% of a population, or the 95% effective dose, the dose that imparts a specific effect in 95% of a population. In some embodiments, efficacy or potency of the formulations comprising NO donors described herein may be improved with the addition of excipients including but not limited to monohydric alcohols, terpenes, terpenoids, isopropyl esters of fatty acids, nonionic surfactants, MPEs, emollients, solubilizing agents, antioxidants, preservatives, chelating agents, organic solvents, antioxidants, or any combination thereof.

As used herein, the term "emollient" refers to an ingredient that soothes or softens skin.

Unless otherwise indicated, the "error bars" provided in the figures represent the standard error of the mean value, whereas the top of the solid, shaded bar represents a single data value, which is the mean value of the distribution of data values.

"Finite dosing" as used herein generally includes an application of a limited formulation dose such as to provide a limited reservoir of an active agent, other agents and chassis. The active agent or one or more other agents in the reservoir is depleted with time, leading to a decrease of the delivery rate after a maximum rate has been reached and perhaps maintained for a period. Similarly, "infinite dosing" as used herein generally includes an application of a substantial formulation dose such as to provide an effectively non-limited reservoir of an active agent, or one or more other agents. The agent(s) in the reservoir is little depleted with time, potentially allowing a delivery rate to be maintained for a longer period.

"Flux" as used herein refers to the amount of a substance delivered into or through a unit area of a membrane in unit time. Flux measurements may be made in vitro using Franz diffusion cells. Suitable membranes for flux studies include synthetic membranes and mammalian skin including human cadaver skin and porcine skin. Flux measurements may also be made in vivo using pharmacokinetic studies and the like.

"Formulation," "pharmaceutical composition," and "composition" as used interchangeably herein are equivalent terms referring to a composition of matter for administration to a subject.

"Gel" as used herein means a semisolid system consisting of either a suspension made up of small inorganic particles or large organic molecules interpenetrated by a liquid. The viscosity of a gel may be such that it is either flowable or non-flowable.

"Irritancy Score" as used herein means a subjective rating of the extent of skin irritation caused by a test composition after such composition is applied to the human forearm. The value of the Irritancy Score ranges from 1 (no detectable irritation) to 10 (severe irritation prompting premature removal of the test composition).

The term "lagtime" or "lag time" as used herein means the x-axis intercept that results from extrapolating the steady-state line of a plot of the cumulative amount of active that has permeated through the membrane or membrane section (y-axis) against time (x-axis). For skin as the membrane, lag time may, as stipulated by the context, refer to permeation through the stratum corneum, through the stratum corneum and epidermis, or through the stratum corneum, epidermis and dermis.

"Lower alcohol" as used herein includes straight- or branched-chain alkyl alcohols with one or more hydroxyl groups that comprise less than seven (7) carbon atoms.

The prefix "micro" as used herein can be alternatively abbreviated as "μ" or "u." For example, micrograms are typically abbreviated as μg, but can alternatively be abbreviated as "ug".

"Monohydric alcohol" as used herein includes straight- or branched-chain alkyl alcohols with a single hydroxyl group.

As used herein the term "multiplexed molecular penetration enhancer" or "MMPE" means a penetration enhancer system comprising two or more substances wherein each of the two or more substances is also a molecular penetration enhancer.

As used herein the term "NO donor" means an agent which is capable of releasing or generating nitric oxide, NO.

The term "onset of action" as used herein means the amount of time it takes for the effects of an active to become noticeable after administration in a formulation to the skin.

The term "or" as used herein should in general be construed non-exclusively. For example, an embodiment of "a composition comprising A or B" would typically present an aspect with a composition comprising both A and B. "Or"

should, however, be construed to exclude those aspects presented that cannot be combined without contradiction (e.g., a composition pH that is between 9 and 10 or between 7 and 8).

The term "organic solvent" as used herein refers to a pure substance or a mixture of substances that is (a) a liquid at an operating temperature such as room temperature, (b) contains at least one carbon atom, and optionally at least one hydrogen atom, and (c) is capable of dissolving another substance to create a solution. Organic solvents have different volatilities. Dimethyl sulfoxide ("DMSO"), for example, has a lower volatility than acetone.

"Penetration enhancer", "chemical penetration enhancer", "molecular penetration enhancer" or "MPE" as used interchangeably herein includes an agent or a combination of agents that improves the transport of molecules such as a pharmaceutically or cosmetically active agent into or through a natural membrane such as skin or nail. A molecular penetration enhancer may be used to assist in the delivery of an active agent topically, regionally, or transdermally. A molecular penetration enhancer may be a pure substance or may comprise a mixture of different chemical entities.

The term "pH adjusting agent" as used herein refers to an agent added to an aqueous solution for the purpose of changing the pH of the solution. Examples of such agents include acids, bases, and buffers that are each pharmaceutically acceptable or cosmetically acceptable. For example, the pH adjusting agent can be an acid, such that when added to an aqueous solution having a pH of 7, will decrease the pH to below 7. The pH adjusting agent can be a base, such that when added to an aqueous solution having a pH of 7, will increase the pH to above 7. The pH adjusting agent can further be a buffer, such that the change in pH caused by a change in composition (such as might be caused by degradation of a formulation ingredient) is reduced relative to that which would otherwise occur in the solution lacking such buffer.

The term "pharmaceutically acceptable" means compatible with the treatment of animals, and in particular, humans. Relative to a pharmaceutically acceptable topical formulation, it is desirable for the formulation to be not irritate or sensitize the skin of a subject to an unacceptable degree; it is also desirable to have chemical and physical stability over a reasonable period, preferably at least two years under typical storage and transportation conditions; it preferably does not include any excipient for which the toxicological properties are not well documented; and it preferably has esthetic attributes that will not discourage use by a subject.

The term "pharmaceutically acceptable salt" means a pharmaceutically acceptable acid addition salt or a pharmaceutically acceptable base addition salt. The formation of a desired compound salt is achieved using standard techniques. For example, the neutral compound is treated with an acid or base in a suitable solvent and the formed salt is isolated by filtration, extraction, or by any other suitable method.

The term "potency" is interpreted herein to mean the specific ability or capacity of the product, as indicated by appropriate laboratory tests or by adequately controlled clinical data obtained through the administration of the product in the manner intended, to effect a given result.

"Regional delivery" as used herein means delivery of an agent through the skin but remaining concentrated in proximate tissue or joint.

"Saturation concentration" of a solute as used herein means the concentration of a solution at which no more the solute will dissolve in the solution.

The term "solubility" as used herein has its ordinary meaning as understood in light of the specification and refers to the ability or extent to which a compound (solute) can dissolve in a solvent. The United States Pharmacopeia and British Pharmacopeia categorize solubility as follows: very soluble, less than 1 parts solvent per 1 part solute; freely soluble, from 1 to 30 parts solvent per 1 part solute; soluble, from 10 to 30 parts solvent per 1 part solute; sparingly soluble, from 30 to 100 parts solvent per 1 part solute; slightly soluble, from 100 to 1000 parts solvent per 1 part solute; very slightly soluble, from 1000 to 10000 parts solvent to 1 part solute; practically insoluble or insoluble, 10000 or more parts solvent per 1 part solute. The solubility properties of an active pharmaceutical ingredient affect its pharmacokinetics and pharmacodynamics, e.g., dissolution rate, transdermal absorption, absorption in the digestive tract, metabolism, excretion and clearance, permeability throughout the body, transit across the blood-brain barrier.

"Solubilizing agent" as used herein means an agent that is added to a solvent system to enhance the solubility of a given active agent in the resulting medium.

As used herein, the term "stability" has its ordinary meaning as understood in light of the specification and refers to the ability for the active compound or the formulation containing the active compound to remain effective, intact, and safe for consumption or administration over time under the influence of environmental factors such as temperature, humidity, and light. Stability can be assessed by forced degradation studies according to parameters, conditions, and standards set forth by the Food and Drug Administration (FDA) and International Council for Harmonization (ICH). In some embodiments, stability of the local anesthetics and formulations comprising a local anesthetic described herein may be improved with the addition of excipients including but not limited to monohydric alcohols, terpenes, terpenoids, isopropyl esters of fatty acids, nonionic surfactants, MPEs, emollients, solubilizing agents, antioxidants, preservatives, chelating agents, organic solvents, or any combination thereof.

"Strength" as used herein when applied to a formulation means the amount of a substance per unit amount of the formulation. For semisolid dosage forms and solutions, the strength of a particular substance can be conveniently characterized as the concentration of the substance usually expressed as a percentage of weight by weight.

The term "subject" as used herein includes all members of the animal kingdom, preferably mammals, and most preferably, humans.

"Superficial delivery" as used herein means delivery of an agent to the skin exterior surface only.

"Surfactant" as used herein includes a surface-active agent. Surfactants reduce the surface tension of a solvent in which they are dissolved.

"Thickening agent" or "viscosity-modifying agent" as used herein includes an agent or combination of agents that increases the viscosity of a composition, potentially without substantially changing its other properties. A thickening agent may be a pure substance, or it may comprise, consist essentially of, or consist of a mixture of different chemical entities.

As used herein, the term "tolerability" has its ordinary meaning as understood in light of the specification and refers to the extent to which a patient will willingly withstand adverse or side effects of an active compound to achieve the desired therapeutic effect and can refer to short-term or long-term side effects. In some embodiments, tolerability of the local anesthetics and formulations comprising a local anesthetic described herein may be improved with the addition of excipients including but not limited to monohydric alcohols, terpenes, terpenoids, isopropyl esters of fatty acids, nonionic surfactants, MPEs, emollients, solubilizing agents, antioxidants, preservatives, chelating agents, organic solvents, or any combination thereof.

"Topical delivery" is used in its conventional sense to mean delivery of an agent, such as a therapeutically active agent, into the viable skin. The outermost layer of the epidermis, the stratum corneum, is lifeless and topical delivery then refers to delivery into the viable epidermis and/or dermis. Topical delivery of a drug may be an advantageous basis, for example, for treatment of various skin disorders. Topical delivery also refers to delivery of an agent into other tissues that are exposed to the environment exterior to the body, such as nail, mucosa or eye.

"Topical formulation" as used herein includes, in one aspect, a composition that is suitable for topical application to the skin, nail, or mucosa. A topical formulation may, for example, be used to confer a therapeutic or cosmetic benefit to its user. Specific topical formulations can be used for superficial, local, regional, or transdermal delivery of substances. The term "topical formulation" as used herein also encompasses the compositions that are formed once a composition that is suitable for topical application to the skin, nail or mucosa is applied to the skin, nail or mucosa. The composition of the topical formulation resulting from such application to the skin, nail or mucosa may differ from the originally applied formulation. For example, components from the originally applied formulation may undergo differential evaporation causing the relative amounts of the ingredients in the formulation to change. Additionally, components from the originally applied formulation may diffuse into the skin, nail or mucosa. Further, compounds that are on or within the substrate to which the formulation is applied may become incorporated into the formulation. For example, linolenic acid and cholesterol, which are natural components of skin, may become incorporated into the formulation.

The term "topical administration" or equivalently "topical application" is used in its conventional sense to mean application of a substance, such as a formulation containing an active agent, to the skin or to a localized more or less external region of the body such as the nail, mucosa or eye. Topical administration may result in any one or more of superficial, topical, regional or transdermal delivery the active agent.

"Transdermal" as used herein includes a process that occurs through the skin. The terms "transdermal," "percutaneous," and "transcutaneous" can be used interchangeably. In certain embodiments, "transdermal" may also include epicutaneous.

"Transdermal delivery" is used in its conventional sense to mean provision of an agent transdermally, that is through the skin, for systemic availability. Following passage through the skin the agent is made available to tissues throughout the body via the lymphatic system and/or the vasculature.

The term "treating" or "treatment" as used herein (and as well understood in the art) means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (e.g., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable. "Treating" and "treatment" as used herein also include prophylactic treatment. Treatment methods comprise administering to a subject a therapeutically effective amount of an active agent. The administering step may consist of a single administration or may comprise a series of administrations. The compositions are administered to the subject in an amount and for a duration sufficient to treat the patient. The length of the treatment period depends on a variety of factors, such as the severity of the condition, the age and genetic profile of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required.

The term "volatility" as used herein refers to the rate at which a substance evaporates. A more volatile organic solvent evaporates more rapidly than a less volatile solvent when each is held at room temperature and pressure.

The term "% weight by weight" "% w/w" or "% wt/wt" means a percentage expressed in terms of the weight of the ingredient or agent over the total weight of the composition multiplied by 100.

Active Ingredients

In some embodiments, the present disclosure provides a pharmaceutically-acceptable composition suitable for topical administration comprising an active ingredient.

In some embodiments, the active ingredient is an NO donor. The NO donor may be an organic NO donor, an inorganic NO donor, a prodrug forms of an NO donor, a compound that can be metabolized in vivo into a compound which delivers NO, or a compound that serves as a physiological precursor of nitric oxide, such as L-arginine and a salt of L-arginine. An NO donor may include at least one organic nitrate (including esters of nitric acid) and can be either a cyclic or acyclic compound.

In some embodiments, the NO donor is nitroglycerin (GTN), isosorbide dinitrate (ISDN), isosorbide mononitrate (ISMN) (which may include isosorbide-2-mononitrate (IS2N) and/or isosorbide-5-mononitrate (IS5N)), erythrityl tetranitrate (ETN), pentaerythritol tetranitrate (PETN), ethylene glycol dinitrate, isopropyl nitrate, glyceryl-1-mononitrate, glyceryl-1,2-dinitrate, glyceryl-1,3-dinitrate, butane-1, 2,4-triol trinitrate, or mixtures thereof.

In some embodiments, the NO donor is sodium nitroprusside, N,O-diacetyl-N-hydroxy-4-chlorobenzenesulfonamide, N(5)-hydroxy-L-arginine (NOHA), hydroxyguanidine sulfate, molsidomine, 3-morpholinosydnonimine (SIN-1), S-nitroso-N-acetylpenicillamine (SNAP), S-nitrosoglutathione (GSNO), (±)-(E)-ethyl-2-[(E)-hydroxyimino]-5-nitro-3-hexeneamide (FK409), (O)—N-[(E)-4-ethyl-3-[(Z)-hydroxyimino]-5-nitro-3-hexen-1-yl]-3-pyridinecarboxamide (FR144420), or 4-hydroxymethyl-3-furoxancarboxamide, or mixtures thereof.

In some embodiments, the NO donor is nitroglycerin (GTN), also known as nitroglycerine, trinitroglycerin, nitro, glyceryl trinitrate, and 1,2,3-trinitroxypropane. In some embodiments, the GTN is converted following topical administration to one or more of 1,2-glyceryl dinitrate (1,2-GDN), nitrate ions, 1,3-dinitroglycerin (1,3-GDN), 1-mononitroglycerin (1-MNG), 2-mononitroglycerin (2-MNG), inorganic nitrite, NO, or S-nitrosothiol (SNO). In some embodiments, measurements of nitroglycerin or a marker thereof may be measured to confirm peak concentrations in a subject's blood plasma. In some embodiments, the blood plasma marker is glycerol dinitrate, 1,2 glycerol dinitrate or 1,3 glycerol dinitrate.

In some embodiments, the composition of the present disclosure comprises organic nitrates similar in size and nitric oxide releasing capacity to nitroglycerin that are also suitable for topical administration such as PETN, ISDN, ISMN, or a 1,2-dialkoxy-2-propyl nitrate.

In some embodiments, the composition of the present disclosure comprises aryl or alkyl nitrites not dissimilar in size and nitric oxide releasing capacity to nitroglycerin that may also be suitable for topical administration such as amyl nitrite.

Other Formulation Constituents

The pharmaceutically-acceptable compositions of the present disclosure may further comprise inactive ingredients. Alternatively, the pharmaceutically-acceptable compositions of the present disclosure may be free of certain inactive ingredients.

In some embodiments, the compositions of the present disclosure are essentially free of hydrocarbon. In some embodiments, the compositions of the present disclosure are essentially free of water.

In some embodiments, the composition further comprises a diluent. In some embodiments nitroglycerin is provided in a diluent. Non-limiting examples of diluents include alcohols, triglycerides such as medium chain triglycerides (MCTs), Miglyol 812, a mixture of caprylic triglyceride and capric triglyceride, and propylene glycol. In some embodiments the diluent is an alcohol. In some embodiments the alcohol is ethanol. In some embodiments the diluent is a mixture of medium chain triglycerides (MCTs), Miglyol 812, or a mixture of caprylic triglyceride and capric triglyceride. In some embodiments the diluent is propylene glycol.

Triglycerides are esters derived from glycerol and three fatty acids. In some instances, these fatty acids are saturated fatty acids, unsaturated fatty acids, or a combination thereof. In some instances, these triglycerides are medium chain triglycerides (MCTs). In some embodiments, these triglycerides comprise medium chain fatty acids.

In some embodiments, the triglycerides are derived from glycerol and medium chain fatty acids. In some embodiments, each medium chain fatty acid independently comprises 6 to 12 carbon atoms in the carbon chain. In some embodiments, each medium chain fatty acid independently comprises 8 to 12 carbon atoms in the carbon chain. In some embodiments, each medium chain fatty acid independently comprises 6, 7, 8, 9, 10, 11, or 12 carbon atoms in the carbon chain. In some embodiments, each medium chain fatty acid independently comprises 8 or 10 carbon atoms in the carbon chain. In some embodiments, the medium chain fatty acids are caproic acid (hexanoic acid), enanthic acid (heptanoic acid), caprylic acid (octanoic acid), pelargonic acid (nonanoic acid), capric acid (decanoic acid), undecylenic acid (undec-O-enoic acid), lauric acid (dodecanoic acid), or a combination thereof. In some embodiments, the medium chain fatty acids are caprylic acid (octanoic acid), capric acid (decanoic acid), or a combination thereof.

In some embodiments, the triglycerides comprising medium chain fatty acids are balassee oil, coconut oil, cohune oil, palm kernel oil, tucum oil, or combinations thereof. In some embodiments, the triglycerides comprising medium chain fatty acids are balassee oil. In some embodiments, the triglycerides comprising medium chain fatty acids are coconut oil. In some embodiments, the triglycerides comprising medium chain fatty acids are cohune oil. In some embodiments, the triglycerides comprising medium chain fatty acids are palm kernel oil. In some embodiments, the triglycerides comprising medium chain fatty acids are tucum oil.

In some embodiments, the diluent is a lower alcohol. In some embodiments, the lower alcohol is ethanol or propylene glycol. In some embodiments, the lower alcohol is propylene glycol.

In some embodiments, the composition further comprises one or more emollients.

In some embodiments, the emollient comprises 1,3-butylene glycol, 1,4-butylene glycol, 2-methyl-1,3-propane diol, 3,4,5-trihydroxybenzoic acid, acetamidopropyl trimonium chloride, acetmonoethanolamide, aloe vera gel, calcium stearoyl lactylate, chitosan pyrrolidone carboxylic acid salt (PCA), citric acid, cyclodextrin, diethylene glycol, diglycerin, diglycerol lactate, dipropylene glycol, d-mannitol, ethyl gallate, ethylene glycol, fructose, fructose ethylene oxide adduct, fructose propylene oxide adduct, galactose, galactose ethylene oxide adduct, galactose propylene oxide adduct, glucosamine, glucose, gluten, glycereth-12, glycereth-26, glycereth-4.5 lactate, glycereth-7, glycerin, glycerol ethylene oxide, glyceryl triacetate, glycolic acid, guanidine, hexadecyl adipate, hexadecyl isostearate, hexadecyl lactate, hexadecyl oleate, hexadecyl stearate, hexylene glycol, honey, hyaluronic acid, hydrolyzed fibronectin, hydrolyzed protein, isodecyl adipate, isodecyl isostearate, isodecyl lactate, isodecyl oleate, isodecyl stearate, isopropyl adipate, isopropyl isostearate, isopropyl lactate, isopropyl oleate, isopropyl stearate, isostearic acid, lactamide MEA, lactic acid, lactose, lactose ethylene oxide adduct, lactose propylene oxide adduct, linoleic acid, lithium chloride, 1-proline, maltitol, maltose, maltose ethylene oxide adduct, maltose propylene oxide adduct, mandelic acid, mannitol, methyl gallate, methyl gluceth-10, methyl gluceth-20, methylsilanol PCA, myristic acid, myristyl adipate, myristyl isostearate, myristyl lactate, myristyl oleate, myristyl stearate, n-(2-hydroxyethyl)lactamide, oleic acid, panthenol, PCA, PEG-4, PEG-8, polyamino sugar condensate, polydextrose, polyethylene glycol, polyglycerin, polyglycerylmethacrylate, polymeric polyols, polyoxyethylene methyl glycoside, propyl gallate, propylene glycol, pyroglutamic acid, pyrrolidone, pyrrolidone carbonate, quaternium-22, quillaia, sea salt, shea butter, sodium adenosine phosphate, sodium capryl lactylate, sodium chondroitin sulfate, sodium hyaluronate, sodium isostearoyl-2-lactylate, sodium lactate, sodium lauroyl lactylate, sodium PEA, sodium polyglutamate, sodium pyroglutamate, sodium pyrrolidonecarboxylate, sodium stearoyl lactylate, soluble collagen, sorbitan laurate, sorbitan oleate, sorbitan sesquiisostearate, sorbitan stearate, sorbitol, sphingolipids, stearic acid, sugar alcohol ethylene oxide adduct, sugar alcohol propylene oxide adduct, tea-PCA, triethylene glycol, urea, vitamin E, xylitol, or a mixture thereof.

In some embodiments, the emollient comprises a fatty acid ester of an alpha hydroxy acid. In some embodiments, the fatty acid ester of an alpha hydroxy acid comprises a C12, C13, C14 or C15 alkyl ester of lactic acid. In some embodiments, the emollient is Ceraphyl 41 (C12-15 alkyl lactate available from Ashland Global Holdings Inc, Wilmington, DE).

In some embodiments, the composition further comprises a fatty acid. In a further embodiment, the fatty acid is oleic acid, isostearic acid, or a mixture thereof.

In some embodiments, the compositions further comprise one or more lubricity-enhancing agents. In some embodiments, the lubricity-enhancing agent is a silicone.

In some embodiments, the composition further comprises one or more MPEs to enhance penetration into biological membranes. MPEs can be grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween 80, nonylphenoxypolyethylene (NP-POE), polysorbates and the like, function as penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcamitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, propylene glycol, polyethylene glycol, glycerol, propanediol and the like) also function as penetration enhancers. In addition, the peptide-like penetration enhancers described in U.S. Pat. Nos. 7,151,191, 6,221,367 and 5,714,167, herein incorporated by references for such disclosure, are contemplated as an additional embodiment. These penetration enhancers are amino-acid and peptide derviatives and enable drug absorption by passive transcellular diffusion without affecting the integrity of membranes or intercellular tight junctions. In some embodiments, a penetration enhancer is hyaluronic acid.

In some embodiments, the MPE is a surfactant. In some embodiments, the MPE is a surfactant comprising an alkyl-glycoside and/or a saccharide alkyl ester. As used herein, an "alkyl-glycoside" means a compound comprising any hydrophilic saccharide (e.g. glucose, fructose, sucrose, maltose, or glucose) linked to a hydrophobic alkyl. In some embodiments, the MPE is a surfactant comprising an alkyl-glycoside wherein the alkyl-glycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the auris acceptable penetration enhancer is a surfactant comprising hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; heptyl- or octyl-1-thio-α- or β-D-glucopyranoside; alkyl thiosucroses; alkyl maltotriosides; long chain aliphatic carbonic acid amides of sucrose β-amino-alkyl ethers; derivatives of palatinose or isomaltamine linked by an amide linkage to an alkyl chain and derivatives of isomaltamine linked by urea to an alkyl chain; long chain aliphatic carbonic acid ureides of sucrose β-amino-alkyl ethers and long chain aliphatic carbonic acid amides of sucrose β-amino-alkyl ethers. In some embodiments, the auris acceptable penetration enhancer is a surfactant comprising an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the MPE is a surfactant comprising an alkyl-glycoside wherein the alkyl glycoside is dodecylmaltoside, tridecylmaltoside, and tetradecylmaltoside. In some embodiments, the auris acceptable penetration enhancer is a surfactant comprising an alkyl-glycoside wherein the alkyl glycoside is tetradecyl-β-D-maltoside. In some embodiments, the MPE is a surfactant comprising an alkyl-glycoside wherein the alkyl-glycoside is a disaccharide with at least one glucose. In some embodiments, the MPE is a surfactant comprising α-D-glucopyranosyl-β-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the MPE is a surfactant comprising an alkyl-glycoside wherein the alkyl-glycoside has a critical miscelle concentration (CMC) of less than about 1 mM in poured water or in aqueous solutions. In some embodiments, the MPE is a surfactant comprising an alkyl-glycoside wherein an oxygen atom within the alkyl-glycoside is substituted with a sulfur atom. In some embodiments, the MPE is a surfactant comprising an alkyl-glycoside wherein the alkylglycoside is the β anomer. In some embodiments, the MPE is a surfactant comprising an alkyl-glycoside wherein the alkylglycoside comprises 90%, 91%, 92%, 93%, 94%, 95%, 96%, 97%, 98%, 99%, 99.1%, 99.5%, or 99.9% of the β anomer.

In certain instances, the MPE is a hyaluronidase. In certain instances, a hyaluronidase is a human or bovine hyaluronidase. In some instances, a hyaluronidase is a human hyaluronidase (e.g., Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase.

In some embodiments the MPE comprises (+/−)-limonene, lauric acid, glycerol, isopropyl alcohol, isopropyl myristate, Transcutol® (di(ethylene glycol) ethyl ether) or azone (1-dodecylazacycloheptan-2-one), a mixture thereof.

In some embodiments, the composition further comprises a viscosity-modifying ingredient. In some embodiments, the viscosity modulating agent is silicon dioxide. In some embodiments, the viscosity modulating agent is a polymer, such as povidone, carbomer, or poloxamer. In some embodiments, the viscosity modulating agent is polyvinyl alcohol (PVA). In some embodiments, the viscosity modulating agent is polyethylene glycol (PEG) based.

In some embodiments, the viscosity-modifying agent is a polysaccharide such as dextran, chitosan, alginic acid, sodium alginate, potassium alginate, ammonium alginate, calcium alginate (polysaccharides from brown algae); agar (polysaccharide obtained from red algae); carrageenan (polysaccharide obtained from red seaweeds); locust bean gum (natural gum polysaccharide from the seeds of the carob tree); pectin (polysaccharide obtained from apple or citrus-fruit); a natural gum, starch, gelatin (made by partial hydrolysis of animal collagen); carbomer polymers, carbomer derivatives, polyvinyl alcohol, poloxamers, as well as mixtures thereof.

In some embodiments, the viscosity-modifying agent is a polymeric or oligomeric derivative of a polymeric carbohydrate that is produced by chemical modification. Representative cellulosic thickening agents include cellulose, hydroxypropyl cellulose ("HPC"), hydroxypropyl methyl cellulose ("HPMC"), hydroxyethyl cellulose ("HEC"), methyl cellulose, carboxymethyl cellulose, hydroxypropylmethylcellulose phthalate, hydroxypropylmethylcellulose acetate stearate (HPMCAS), noncrystalline cellulose and the like.

In some embodiments, the viscosity-modifying agent is selected from hydroxypropyl cellulose, polyoxyethylene sorbitan monooleate, acrylamide/sodium acryloyldimethyl taurate copolymer, or a mixture thereof. In some embodiments, the composition comprises a viscosity-modifying ingredient that is HPC. In a further embodiment, the HPC is HY119 (Spectrum Chemical Mfg. Corp., New Brunswick, NJ) or Klucel® (Ashland Global Holdings Inc, Wilmington, DE).

In some embodiments, the composition comprises a viscosity-modifying ingredient that is a mixture of acrylamide acryloyldimethyl taurate copolymer, isohexadecane and polysorbate 80. In certain embodiments, such viscosity-modifying ingredient is provided as a compounded mixture such as the thickening, emulsifying and stabilizing polymer sold under the trade name SEPINEO™ P 600 (Seppic Inc., Fairfield New Jersey). SEPINEO P 600 is typically used in water-containing formulations. Surprisingly, it was found that SEPINEO P 600 functions effectively in essentially water-free compositions of the present disclosure.

A free-flowing solution is inconvenient to administer to a substantial area of skin, particularly an area of skin covering the hands or feet. A light gel formulation, on the other hand, is more convenient to spread over the hand and fingers, and foot and toes. A gel formulation, such as a light gel or a heavy gel, further has better substantivity than a low-viscosity solution. The viscosity-modifying ingredient may function as a gelling agent. However, there may be no requirement for the addition of a viscosity-modifying ingredient if other components in the composition are capable of acting as a gelling agent.

In some embodiments, the viscosity-modifying agent is gelling agent, able to dissolve in the liquid phase as a colloid mixture that forms a weakly cohesive internal structure.

In some embodiments, the viscosity-modifying agent acts as mechanical thixotropic additive with discrete particles adhering or interlocking to resist strain.

In some embodiments, compositions of the present disclosure may further comprise a lower alcohol. Suitable lower alcohols include methanol, n-propanol, isopropanol, n-butanol, t-butanol, n-pentanol, 3-pentanol, n-hexanol, 2-methoxyethanol, 2-(2-ethoxyethoxy)ethanol, propylene glycol (propane-1,2-diol), butanediol, butynediol, pentanediol, hexanediol, hexane triol and the like.

In some embodiments, compositions of the present disclosure may further comprise a monohydric alcohol. Suitable monohydric alcohols include methanol, n-propanol, isopropanol, n-butanol, t-butanol, n-pentanol, 3-pentanol, n-hexanol, 2-methoxyethanol, 2-(2-ethoxyethoxy)ethanol, hexadecan-1-ol, oleyl alcohol, isostearyl alcohol and the like.

In some embodiments, compositions of the present disclosure may further comprise an antimicrobial agent. Suitable antimicrobials include methyl paraben, ethyl paraben, propyl paraben, butyl paraben, benzyl alcohol, chlorobutanol, phenol, 1-dodecylazocyloheptan-2-one, N-methylpyrrolidone, N-hydroxyethylpyrrolidone, N-cyclohexylpyrrolidone, N-dimethylaminopropylpyrrolidone, N-cocoalkylpyrrolidone, N-tallowalkylpyrrolidone, benzylkonium chloride, and benzethonium chloride and the like.

In some embodiments, compositions of the present disclosure may further comprise an antioxidant. Suitable antioxidants include ascorbic acid, ascorbyl linoleate, ascorbyl dipalmitate, ascorbyl palmitate, ascorbyl tocopherol maleate, butylated hydroxytoluene (BHT), butylated hydroxyanisole (BHA) and tocopherol acetate. The antioxidant may also be an antimicrobial agent.

In some embodiments, the composition further comprises an agent that indicates to which area of the skin a topical has been applied (e.g. marking agent). In some embodiments, the marking agent is a colorant.

Compositions

Descriptions of the ranges and values provided below are for illustration purposes only, and do not otherwise limit the scope of the disclosed subject matter.

In certain embodiments, the present disclosure provides compositions of an active (e.g. nitroglycerin) that are suitable for topical administration. In certain embodiments, the topical compositions are prepared using a formulation of an active in a diluent that is suitable for use in a pharmaceutical preparation. In certain embodiments, the topical compositions are prepared using a solution of the active in propylene glycol. In certain embodiments, the topical compositions are prepared using a solution of about 1 to about 25% w/w of the active in propylene glycol. In some embodiments the solution is about 10% w/w of the active in propylene glycol.

In certain embodiments, the active is present in the topical formulation at about 0.5 to 10% w/w. In some embodiments, the active is present in the topical formulation at about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5 or about 9.0% w/w such that each 1 gram of the topical formulation contains, respectively, approximately about 10, about 15, about 20, about 25, about 30, about 35, about 40, about 45, about 50, about 55, about 60, about 65, about 70, about 75, about 80, about 85 or about 90 mg of the active. In some embodiments, the active is present at 3% or more, 4% or more, 5% or more, 6% or more, 7% or more, or 8% or more w/w. In a further embodiment, the active is present in the topical formulation at 8.0% w/w such that each 1 gram of the topical formulation contains 80 mg of the active.

In certain embodiments, the topical formulation is a single-phase solution. In certain embodiments, the topical formulation is a single-phase viscous solution. In certain embodiments, the topical formulation is a single-phase gelled solution.

In certain embodiments, a viscosity-modifying ingredient (e.g. hydroxypropyl cellulose) is present in the topical formulation at about 0.5 to 10% w/w. In some embodiments, a viscosity-modifying ingredient is present in the topical formulation at about 0.5, about 1.0, about 1.5, about 2.0, about 2.5, about 3.0, about 3.5, about 4.0, about 4.5 or about 5.0% w/w. In some embodiments, a viscosity-modifying ingredient is present in the topical formulation at about 3.0% w/w.

In certain embodiments, a viscosity-modifying ingredient (e.g. SEPINEO P600) is present in the topical formulation at about 0.5 to 10% w/w. In some embodiments a viscosity-modifying ingredient is present in the topical formulation at about 0.5, 1.0, 1.5, 2.0, 2.5, 3.0, 3.5, 4.0, 4.5, 5.0, 5.5, 6.0 or 6.5% w/w. In some embodiments, a viscosity-modifying ingredient is present in the topical formulation at about 4.0% w/w.

In some embodiment, the topical formulation disclosed herein have greater viscosity than an aqueous liquid formulation. In some embodiment, the topical formulation disclosed herein have lower viscosity than a hydrocarbon-based ointment formulation. In some embodiments, the formulation has a viscosity of greater than 1 cP (centipoise). In some embodiments, the formulation has a viscosity of at least about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 2,000 cP, about 3,000 cP, about 4,000 cP, about 5,000 cP, about 6,000 cP, about 7,000 cP, about 8,000 cP, about 9,000 cP, about 10,000 cP, about 15,000 cP, or about 20,000 cP. In some embodiments, the formulation has a viscosity of less than about 1,000 cP. In some embodiments, the formulation has a viscosity of less than about 10,000 cP. In some embodiments, the formulation has a viscosity of about 2 cP to about 250,000 cP, about 2 cP to about 100,000 cP, about 2 cP to about 50,000 cP, about 2 cP to about 25,000 cP, about 2 cP to about 10,000 cP, about 2 cP to about 5,000 cP, about 2 cP to about 1,000 cP, about 2 cP to about 500 cP, about 2 cP to about 250 cP, about 2 cP to about 100 cP, about 2 cP to about 90 cP, about 2 cP to about 80 cP, about 2 cP to about 70 cP, about 2 cP to about 60 cP, about 2 cP to about 50 cP, about 2 cP to about 40 cP, about 2 cP to about 30 cP, about 2 cP to about 20 cP, or about 2 cP to about 10 cP. In some embodiments, the liquid formulation has a viscosity of about 2 cP, about 5 cP, about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 5,000 cP, about 10,000 cP, about 20,000 cP, about 50,000 cP, about 100,000 cP, or about 250,000 cP.

In some embodiments, the formulation has a viscosity between about 10 cP to about 20,000 cP. In some embodiments, the formulation has a viscosity between about 10 cP to about 10,000 cP. In some embodiments, the formulation has a viscosity between about 10 cP to about 5,000 cP. In some embodiments, the formulation has a viscosity between about 10 cP to about 1,000 cP. In some embodiments, the formulation has a viscosity between about 10 cP to about 500 cP. In some embodiments, the formulation has a viscosity between about 10 cP to about 250 cP. In some embodiments, the formulation has a viscosity between about 10 cP to about 100 cP. In some embodiments, the formulation has a viscosity between about 10 cP to about 50 cP.

In some embodiments, the formulation has a viscosity of about 10 cP. In some embodiments, the formulation has a viscosity of about 20 cP. In some embodiments, the formulation has a viscosity of about 30 cP. In some embodiments, the formulation has a viscosity of about 40 cP. In some embodiments, the formulation has a viscosity of about 50 cP. In some embodiments, the formulation has a viscosity of about 60 cP. In some embodiments, the formulation has a viscosity of about 70 cP. In some embodiments, the formulation has a viscosity of about 80 cP. In some embodiments, the formulation has a viscosity of about 90 cP. In some embodiments, the formulation has a viscosity of about 100 cP. In some embodiments, the formulation has a viscosity of about 150 cP. In some embodiments, the formulation has a viscosity of about 200 cP. In some embodiments, the formulation has a viscosity of about 250 cP. In some embodiments, the formulation has a viscosity of about 300 cP. In some embodiments, the formulation has a viscosity of about 350 cP. In some embodiments, the formulation has a viscosity of about 400 cP. In some embodiments, the formulation has a viscosity of about 450 cP. In some embodiments, the formulation has a viscosity of about 500 cP. In some embodiments, the formulation has a viscosity of about 550 cP. In some embodiments, the formulation has a viscosity of about 600 cP. In some embodiments, the formulation has a viscosity of about 650 cP. In some embodiments, the formulation has a viscosity of about 700 cP. In some embodiments, the formulation has a viscosity of about 750 cP. In some embodiments, the formulation has a viscosity of about 800 cP. In some embodiments, the formulation has a viscosity of about 850 cP. In some embodiments, the formulation has a viscosity of about 900 cP. In some embodiments, the formulation has a viscosity of about 950 cP. In some embodiments, the formulation has a viscosity of about 1,000 cP. In some embodiments, the formulation has a viscosity of about 1,500 cP. In some embodiments, the formulation has a viscosity of about 2,000 cP. In some embodiments, the formulation has a viscosity of about 2,500 cP. In some embodiments, the formulation has a viscosity of about 3,000 cP. In some embodiments, the formulation has a viscosity of about 3,500 cP. In some embodiments, the formulation has a viscosity of about 4,000 cP. In some embodiments, the formulation has a viscosity of about 4,500 cP. In some embodiments, the formulation has a viscosity of about 5,000 cP. In some embodiments, the formulation has a viscosity of about 5,500 cP. In some embodiments, the formulation has a viscosity of about 6,000 cP. In some embodiments, the formulation has a viscosity of about 6,500 cP. In some embodiments, the formulation has a viscosity of about 7,000 cP. In some embodiments, the formulation has a viscosity of about 7,500 cP. In some embodiments, the formulation has a viscosity of about 8,000 cP. In some embodiments, the formulation has a viscosity of about 8,500 cP. In some embodiments, the formulation has a viscosity of about 9,000 cP. In some embodiments, the formulation has a viscosity of about 9,500 cP. In some embodiments, the formulation has a viscosity of about 10,000 cP. In some embodiments, the formulation has a viscosity of about 20,000 cP.

In some embodiments, the formulation is free or substantially free of viscosity modulating agent. In some embodiments, the formulation contains at least one viscosity modulating agent that provides a viscosity of at least about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1000 cP, about 2,000 cP, about 3,000 cP, about 4,000 cP, about 5,000 cP, about 6,000 cP, about 7,000 cP, about 8,000 cP, about 9,000 cP, about 10,000 cP, about 15,000 cP, or about 20,000 cP. In some embodiments, the formulation contains at least one viscosity modulating agent that provides a viscosity of less than about 1,000 cP. In some embodiments, the formulation contains at least one viscosity modulating agent that provides a viscosity of less than about 10,000 cP. In some embodiments, the formulation contains at least one viscosity modulating agent that provides a viscosity of about 2 cP to about 250,000 cP, about 2 cP to about 100,000 cP, about 2 cP to about 50,000 cP, about 2 cP to about 25,000 cP, about 2 cP to about 10,000 cP, about 2 cP to about 5,000 cP, about 2 cP to about 1,000 cP, about 2 cP to about 500 cP, about 2 cP to about 250 cP, about 2 cP to about 100 cP, about 2 cP to about 90 cP, about 2 cP to about 80 cP, about 2 cP to about 70 cP, about 2 cP to about 60 cP, about 2 cP to about 50 cP, about 2 cP to about 40 cP, about 2 cP to about 30 cP, about 2 cP to about 20 cP, or about 2 cP to about 10 cP. In some embodiments, the formulation contains at least one viscosity modulating agent that provides a viscosity of about 2 cP, about 5 cP, about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 5,000 cP, about 10,000 cP, about 20,000 cP, about 50,000 cP, about 100,000 cP, or about 250,000 cP.

In certain embodiments, the topical formulation has a viscosity of 500-5000 centipoise. In some embodiments, the formulation has a viscosity of less than 10,000 centipoise.

In some embodiment, the formulation further comprises a pH adjusting agent, a buffering agent, or both to provide suitable pH range for topical application, e.g. skin tolerable. In some embodiments, the formulation has a pH of from about 2 to about 9. In some embodiments, the formulation has a pH of from about 2 to about 8. In some embodiments, the formulation has a pH of from about 2.5 to about 8. In some embodiments, the formulation has a pH of from about 3 to about 8. In some embodiments, the formulation has a pH of from about 3.5 to about 8. In some embodiments, the formulation has a pH of from about 3.5 to about 7. In some embodiments, the formulation has a pH of from about 4 to about 6.5. In some embodiments, the formulation has a pH of between about 4 to about 6. In some embodiments, the formulation has a pH of from about 4 to about 5.5. In some embodiments, the formulation has a pH of from about 4.5 to about 5.5. In some embodiments, the formulation has a pH of from about 4.8 to about 5. In some embodiments, the formulation has a pH of about 4. In some embodiments, the formulation has a pH of about 4.2. In some embodiments, the formulation has a pH of about 4.4. In some embodiments, the formulation has a pH of about 4.6. In some embodiments, the formulation has a pH of about 4.8. In some embodiments, the formulation has a pH of about 5. In some embodiments, the formulation has a pH of about 5.2. In some embodiments, the formulation has a pH of about 5.4. In some embodiments, the formulation has a pH of about 5.6. In some embodiments, the formulation has a pH of about 5.8. In some embodiments, the formulation has a pH of about 6.

In certain embodiments, the topical formulation includes a diluent (e.g. propylene glycol) at up to 90% w/w. In certain embodiments, the topical formulation includes at least about 50% w/w, at least about 60% w/w or at least about 70% w/w of a diluent. In certain embodiments, the topical formulation includes propylene glycol at 65-85% w/w, or about 65, 75, 80, or 85% w/w.

In certain embodiments, the topical formulation includes an emollient. In certain embodiments, the emollient is a fatty acid ester of an alpha hydroxy acid. In certain embodiments, the emollient is present at about 0.5 to 5% w/w or about 0.5, 1.0, 1.5, 2.0, 2.5, 3.0, 3.5, 4.0% or 5.0% w/w. In certain embodiments, the emollient is present at up to about 2% w/w. In certain embodiments, the emollient is Ceraphyl 41. In certain embodiments, the Ceraphyl 41 is present at about 1.5% w/w.

In certain embodiments, the topical formulation further comprises a fatty acid. In certain embodiments, the fatty acid is present at about 1 to 15% w/w or at about 1.0, 2.0, 3.0, 4.0, 5.0, 6.0, 7.0, 8.0, 9.0, 10.0, 11.0, 12.0, 13.0, 14.0 or 15.0% w/w. In certain embodiments, the fatty acid is present at about 9.0, 10.0, 11.0, 12.0 or 13.0% w/w. In certain embodiments, the fatty acid is oleic acid or isostearic acid. In certain embodiments, the fatty acid is oleic acid. In certain embodiments, the oleic acid is present at about 8%, 9% 10%, 11% or 12.0% w/w. In certain embodiments, the fatty acid is isostearic acid. In certain embodiments, the isostearic acid is present at about 10.0% w/w.

In certain embodiments, the topical formulation further includes a lubricity-enhancing agent. In certain embodiments, the lubricity-enhancing agent is present at about 0.1 to 5% w/w/or about 0.25, 0.5, 0.75, 1.0, 1.5 or 2.0% w/w. In certain embodiments, the lubricity-enhancing agent is a cyclic siloxane. In certain embodiments, the cyclic siloxane is cyclomethicone. In certain embodiments, the cyclomethicone is present at about 0.5% w/w.

In certain embodiments, the topical formulation further includes an MPE. In certain embodiments, the MPE is present at about 0.25 to 15% w/w or about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0% or w/w. In certain embodiments, the MPE is present at about 6.0, 7.0, 8.0, 9.0, or 10.0% w/w. In certain embodiments, the MPE is Brij L4, isopropyl myristate, isopropyl palmitate, dimethyl isosorbide, di(ethylene glycol) ethyl ether (Transcutol), or mixtures thereof. In certain embodiments, Brij L4 is present at about 4.0% w/w.

In some embodiments, the composition comprises an active agent, a diluent, a fatty acid, an emollient, a lubricity-enhancing agent, a viscosity-modifying agent and, optionally, an MPE. In some embodiments, the composition comprises about 0.5 to 10% w/w of an active agent, at least about 50% w/w of a diluent, about 1 to 15% w/w of a fatty acid, about 0.5 to 5% w/w of an emollient, about 0.1 to 5% w/w of a lubricity-enhancing agent, about 0.5 to 10% w/w of a viscosity-modifying agent, and optionally about 0.25 to 15% w/w of an MPE.

In some embodiments, the composition comprises: an active agent selected from nitroglycerin (GTN), pentaerythritol tetranitrate (PETN), isosorbide dinitrate (ISDN), isosorbide mononitrate (ISMN), or a 1,2-dialkoxy-2-propyl nitrate, or a mixture thereof, a diluent selected from alcohols, medium chain triglycerides, Miglyol 812, a mixture of caprylic triglyceride and capric triglyceride, or propylene glycol; a fatty acid selected from oleic acid or isostearic acid; an emollient that is a fatty acid ester of lactic acid comprising a C12, C13, C14 or C15 alkyl ester of lactic acid; a lubricity-enhancing agent selected from a silicone or cyclic siloxane; a viscosity-modifying agent selected from hydroxypropyl cellulose, polyoxyethylene sorbitan monooleate, acrylamide/sodium acryloyldimethyl taurate copolymer or a mixture thereof, and optionally an MPE selected from Brij L4, isopropyl myristate, isopropyl palmitate, dimethyl isosorbide, di(ethylene glycol) ethyl ether or a mixture thereof.

In some embodiments, the composition comprises:
(i) about 0.5 to 10% w/w nitroglycerin;
(ii) at least 50% w/w propylene glycol;
(iii) about 1 to 15% w/w oleic acid or isostearic acid;
(iv) optionally, about 0.5 to 5% w/w Ceraphyl 41;
(v) about 0.1 to 5% w/w cyclomethicone;
(vi) about 0.5 to 10% w/w hydroxypropyl cellulose or SEPINEO P 600;
(vii) optionally about 0.25 to 15% w/w Brij L4, isopropyl myristate, dimethyl isosorbide, di(ethylene glycol) ethyl ether or a mixture thereof, and
(viii) optionally about 0.05 to 0.80% of butylated hydroxytoluene.

In some embodiments there is provided a topical formulation of nitroglycerin suitable for causing vasodilation in the body extremities of a subject promptly following administration to the skin of the body extremities.

In some embodiments there is provided a topical formulation of nitroglycerin suitable for causing vasodilation in the body extremities of a subject without causing a headache in such subject.

In some embodiments there is provided a pharmaceutically-acceptable topical formulation of nitroglycerin that is essentially free of both water and hydrocarbon and which comprises more than 4% w/w of nitroglycerin.

In some embodiments there is provided a pharmaceutically-acceptable topical formulation of nitroglycerin that is essentially free of both water and hydrocarbon and which comprises more than 30% w/w of propylene glycol.

In some embodiments there is provided a pharmaceutically-acceptable topical formulation of nitroglycerin that is essentially free of both water and hydrocarbon and which further comprises a viscosity-modifying agent.

In some embodiments there is provided a pharmaceutically-acceptable topical formulation of nitroglycerin that is essentially free of both water and hydrocarbon and which comprises more than 4% w/w of nitroglycerin, more than 30% w/w of propylene glycol and one or more of hydroxypropyl cellulose, polyoxyethylene sorbitan monooleate or acrylamide/sodium acryloyldimethyl taurate copolymer.

In some embodiments there is provided a pharmaceutically-acceptable topical formulation of nitroglycerin that is essentially free of both water and hydrocarbon and which comprises more than 4% w/w of nitroglycerin, SEPINEO™ P 600 and more than 30% w/w of propylene glycol.

In some embodiments there is provided is a pharmaceutically-acceptable topical formulation of nitroglycerin that is essentially free of both water and hydrocarbon and which comprises more than 4% w/w of nitroglycerin, more than 30% w/w of propylene glycol, one or more of hydroxypropyl cellulose, polyoxyethylene sorbitan monooleate or acrylamide/sodium acryloyldimethyl taurate copolymer, and oleic acid.

In some embodiments there is provided a pharmaceutically-acceptable topical formulation of nitroglycerin that is essentially free of both water and hydrocarbon and which comprises more than 4% w/w of nitroglycerin, more than 30% w/w of propylene glycol, one or more of hydroxypropyl cellulose, polyoxyethylene sorbitan monooleate or acrylamide/sodium acryloyldimethyl taurate copolymer, oleic acid, and a C12, C13, C14 or C15 alkyl ester of lactic acid.

In some embodiments there is provided a pharmaceutically-acceptable topical formulation of nitroglycerin that is essentially free of both water and hydrocarbon and which comprises more than 4% w/w of nitroglycerin, more than 30% w/w of propylene glycol, one or more of hydroxypropyl cellulose, polyoxyethylene sorbitan monooleate or acrylamide/sodium acryloyldimethyl taurate copolymer, oleic acid, and butylated hydroxytoluene.

In some embodiments of the disclosure there is provided a pharmaceutically-acceptable topical formulation of nitroglycerin that is essentially free of both water and hydrocarbon and which comprises more than 4% w/w of nitroglycerin, more than 30% w/w of propylene glycol, and one or more of hydroxypropyl cellulose, polyoxyethylene sorbitan monooleate or acrylamide/sodium acryloyldimethyl taurate copolymer that is suitable for marketing approval in the United States through a new drug application according to section 505(b)(2) of the Federal Food, Drug, and Cosmetic Act.

Method of Manufacture

In some embodiments of the disclosure there is provided a method of manufacturing a topical formulation of nitroglycerin that is essentially free of both water and hydrocarbon and which comprises more than 4% w/w of nitroglycerin, more than 30% w/w of propylene glycol comprising: (i) providing appropriate amounts of all excipients other than diluent and viscosity-modifying agent into a vessel, (ii) providing the appropriate amount of nitroglycerin dissolved in a suitable diluent into said vessel, (iii) agitating the mixture in said vessel until homogeneous, (iv) providing into said vessel the appropriate quantity of viscosity-modifying agent, and (v) mixing the combination thoroughly.

Permeation & Stability

In certain embodiments, the topical formulation provides a cumulative amount of organic nitrate (being the sum of GTN, 1,2-GDN, 1,3-GDN, 1-MNG and 2-MNG), through partial thickness human cadaver skin in a permeation study using Franz-type vertical diffusion cells that is about 1, 2, 3, 4, 5, 6, 7, 8, 9, 10 or greater than 10 fold higher than that provided in a direct comparison by nitroglycerin USP 2 wt. % ointment.

In certain embodiments, the topical formulation is chemically stable, such that the nitroglycerin degrades by less than 5% over the course of 6 months under ambient conditions.

In certain embodiments, the topical formulation is chemically stable, such that the nitroglycerin degrades by less than 2.5% over the course of 6 months under ambient conditions.

In certain embodiments, the topical formulation is chemically stable, such that the nitroglycerin degrades by less than 1% over the course of 6 months under ambient conditions.

In certain embodiments, the topical formulation is chemically stable, such that the nitroglycerin degrades by less than 5% over the course of 6 months at 40° C.

In certain embodiments, the topical formulation is physically stable, such that after 6 months under ambient conditions, the topical formulation is substantially clear and includes less than 5% w/w of solid material.

In certain embodiments, the topical formulation is physically stable, such that after 6 months under ambient conditions, the topical formulation is substantially clear and includes less than 1% w/w of solid material.

In certain embodiments, upon topical application the topical formulation has a drying rate that results in a residue of no more than 50% of the weight of formulation applied at a dose of 4.0 µL cm$^{-2}$ after 2 hours under ambient conditions.

In certain embodiments, upon topical application the topical formulation has a drying rate that results in a residue of no more than 25% of the weight of formulation applied at a dose of 4.0 µL cm$^{-2}$ after 2 hours under ambient conditions.

In certain embodiments, upon topical application the topical formulation has a drying rate that results in a residue of no more than 10% of the weight of formulation applied at a dose of 4.0 µL cm$^{-2}$ after 2 hours under ambient conditions.

Container-Closure Systems and Dispensation

In certain embodiments, the compositions of the present disclosure are provided in an enclosure system. In certain embodiments, the enclosure system is a tube, bottle, spray bottle, pump bottle, sachet or jar or other container similar to one used previously for a drug product approved by the FDA, which may contain one or more unit dosage forms containing the active ingredient.

In certain embodiments, the compositions of the present disclosure may be placed in an appropriate container, and labeled for treatment of an indicated condition.

Kits

The compositions of the present disclosure may be provided as a kit. In certain embodiments, the kit comprises a pack or dispenser comprising a composition of the present disclosure and may be further accompanied by a notice associated with the container in a form prescribed by a governmental agency regulating the manufacture, use or sale of pharmaceuticals, which notice indicates approval by the agency of the form of the compositions for human or veterinary administration. Such notice, for example, may comprise labeling approved by the U.S. Food and Drug Administration for prescription drugs, or of an approved product insert.

In certain embodiments, the compositions of the present disclosure are provided in a suitable container, generally together with instructions that direct how the composition is to be applied to a subject. In certain embodiments, the composition is accompanied by instructions as to how much of said topical formulation of nitroglycerin is to be administered according to the hand size of the subject. In certain embodiments, the compositions of the disclosure are accompanied by instructions advising that the topical formulation of nitroglycerin is not to be transported by air.

In certain embodiments, the composition or formulation of the present disclosure is not incorporated or impregnated into a skin contact support member. In certain embodiments, the composition or formulation of the present disclosure is not incorporated or impregnated into a skin compatible patch, such as a transdermal patch. Without wishing to be bound by any particular theory, it is contemplated that in certain embodiments the physical characteristics of the composition or formulation disclosed herein allows it to be applied to the skin, and spread over the area of skin of the subject to be treated without occluding said treated skin area with a support member, such as a transdermal patch.

In certain embodiments, the composition or formulation of the present disclosure is incorporated or impregnated into a skin contact support member. In certain embodiments, the composition or formulation of the present disclosure is incorporated or impregnated into a skin compatible patch, such as a transdermal patch. Without wishing to be bound by any particular theory, it is contemplated that in certain embodiments the physical characteristics of the composition or formulation disclosed herein allows it to be retained in the support member before the formulation is applied to the skin, and secured over the area of skin of the subject to be treated.

METHODS OF USE

The compositions of the present disclosure may be useful in treating one or more diseases, disorders or conditions. In some embodiments, the compositions of the present disclosure may be self-administered by a subject or applied to a subject by a trained medical professional.

In some embodiments, the methods of treating a disease, disorder or condition, comprise topically administering a composition comprising the active ingredient, or pharmaceutically acceptable salts, solvates, metabolites, derivatives, or prodrugs thereof. In some embodiments, the compositions of the present disclosure may be dispensed in a suitable quantity from a container, applied to the skin, and spread more or less uniformly over the area of skin of the subject to be treated.

In some embodiments, the compositions of the present disclosure may be administered once a day, twice a day, three times a day, four times a day, or as needed. Compositions of the present disclosure may be administered less frequently than daily, or not according to a regular schedule. In some embodiments, the compositions are administered once a day in the morning. In some embodiments, the last application of the topical formulation is at least two, three, four, five or six hours before the subject's bedtime. In some embodiments, the timing of administration of the formulation is indicated to the subject by a device worn by the subject.

In some embodiments, the compositions of the present disclosure are suitable for acute and/or chronic use by a subject.

In some embodiments, the topical formulation of nitroglycerin provides no warming sensation when applied to the skin of said subject. In some embodiments, the topical formulation of nitroglycerin provides no cooling sensation when applied to the skin of said subject.

Suitable areas of skin to which a composition of the present disclosure will be administered generally depend on the nature of the condition and on the area of the body which is affected by the condition being treated. In some embodiments, a suitable area may range from 50 cm$^2$ to 800 cm$^2$. In some embodiments, the area can range from 100 cm$^2$ to 600 cm$^2$.

Suitable amounts per administration will generally depend on the area of the body which is affected by the condition being treated. In some embodiments, a suitable amount may range from 0.5 μL cm$^{-2}$ to 8.0 L cm$^{-2}$. In some embodiments, the amount can range from 2.0 to 4.0 μL cm$^{-2}$. In some embodiments the topical formulation of nitroglycerin is applied to the subject at a dose per unit area of no more than 10 mg cm$^{-2}$.

In certain embodiments, the topical formulation is applied to clean, dry skin. In some embodiments, the topical formulation is applied to the hand of the subject. In some embodiments, the topical formulation is applied to the foot of the subject. In some embodiments, the topical formulation is applied both to the hand and the foot of the subject. In some embodiments, no more than 200 μL of the topical formulation is applied to a hand of the subject.

In certain embodiments, the topical formulation is (i) dispensed directly onto a hand, or first into one hand and then onto the other hand, and (ii) spread evenly around the front, back and sides of the hand.

In certain embodiments, the topical formulation is (i) dispensed directly onto a foot, or first into one hand and then onto either or both feet, and (ii) spread evenly around the front, back and sides of the foot or feet, and (iii) both hands are washed thoroughly.

In certain embodiments, the topical formulation is (i) dispensed directly onto a hand, or first onto one hand by which it is then applied to the other hand, and (ii) spread evenly around the front, back and sides of the hand, and (iii) the subject waits until the areas of administration are dry before (a) covering the area with clothing, or (b) topically applying to the area sunscreen, insect repellent, cosmetics, or another topical medication, or (c) making skin-to-skin contact between the treated body extremity and another person.

In certain embodiments, a subject is instructed to apply the topical formulation at least ten minutes prior to commencing an activity which is likely to cause compromise of peripheral blood flow. In certain embodiments, the application is realized without a requirement for one or more of: (i) said formulation coming into contact with the skin of the other hand; (ii) rubbing said formulation into the skin; (iii) spreading said formulation by other than the container in which said topical formulation is provided.

In certain embodiments, the subject is able to hold their hand to which the topical formulation of nitroglycerin is applied in ice water for a period that is at least 50% longer after said administration than prior to said administration.

In certain embodiments, the composition is provided together with instructions advising that the amount of said topical formulation of nitroglycerin applied to a hand is to be adjusted based on the size of the hand or the size of the digits.

In certain embodiments, the composition is applied to a hand of said subject, said subject handwrites on paper with said hand in an uncovered state within 20 minutes of said topical administration, and no transference of remnant topical formulation is visible on said paper.

Methods of Treatment

Compositions of the present disclosure are particularly suited for use in treating one or more diseases, disorders or conditions. In some embodiments of the disclosure provided is a use of the formulation for topical administration to a subject in need thereof.

In some embodiments, the compositions of the disclosure are useful to treat Raynaud's phenomenon, or useful in preventing or reducing the severity of episodes of Raynaud's phenomenon.

In some embodiments, the compositions of the present disclosure are useful for the treatment of other conditions in which peripheral blood flow is compromised.

In some embodiments, the compositions of the present disclosure are useful for the treatment or amelioration of one or more symptoms of primary Raynaud's or secondary Raynaud's phenomenon associated with one or more of systemic sclerosis, CREST syndrome, systemic lupus erythematosus, rheumatoid disease, rheumatoid arthritis, Sjogren's syndrome, polymyositis or autoimmune disease.

In some embodiments, the compositions of the present disclosure are useful for the treatment or amelioration of one or more symptoms of traumatic edema.

In some embodiments, the compositions of the present disclosure are useful for the treatment of chronic tendinopathies, mastectomy skin flap necrosis, autonomic dysreflexia associated with spinal cord injury, intraoperative microsurgical vasospasm, chondrodermatitis nodularis helicis, chronic anal fissure, introital dyspareunia and vulvar pain in women with vulvodynia.

In some embodiments, the compositions of the present disclosure are useful for causing radial artery vasodilation prior to cannulation.

In some embodiments, the compositions of the present disclosure are useful for the treatment or amelioration of one or more symptoms associated with peripheral artery disease, peripheral vascular disease, diabetic neuropathy, tendinopathy, erectile dysfunction, alopecia, male pattern baldness and female pattern baldness.

In some embodiments, the compositions of the present disclosure are useful for the treatment or amelioration of pain in a female subject associated with breastfeeding arising from diminished blood flow to the nipple region.

In some embodiments, the compositions of the present disclosure may be administered prior to a subject being exposed to a circumstance that might lead to peripheral blood flow being compromised. In some embodiments the disclosure provides a method for treating a condition in a subject in which peripheral blood flow is compromised.

In some embodiments, the compositions of the present disclosure may be administered to prevent compromised peripheral blood flow, that is prophylactically.

In some embodiments, the compositions of the present disclosure may be administered to treat compromised peripheral blood flow or the symptoms of compromised peripheral blood flow. In some embodiments, the symptom comprises skin redness, cyanosis of the skin, skin blanching, low skin temperature, pain in the hands or feet, numbness in the hands or feet, tingling in the hands or feet, parasthesia, throbbing in the hands or feet, and the number of Raynaud's attacks in the hands or feet.

In some embodiments, the subject has a likelihood or severity of headache that is reduced relative to that which accompanies application to the skin of said subject of 2% nitroglycerin ointment USP according to the label directions for the treatment of angina pectoris.

The present disclosure further provides for a method for treating peripheral ischemic episodes in a subject.

In some embodiments, the method includes topically administering to the fingers of the subject a therapeutically effective amount of the topical formulation described herein.

In some embodiments, the methods of treatment of the disclosure provide a blood plasma level of nitroglycerin or marker thereof such as glycerol dinitrate that is less than that realized following administration of USP 2% ointment according to the label directions.

In some embodiments, a single instance of topical administration of a composition of the present disclosure results in a peak concentration of nitroglycerin in the blood plasma of said subject no greater than that realized following administration of USP 2% ointment according to the label directions. In some embodiments, a single instance of topical administration of a composition of the present disclosure results in a peak concentration of 1,2 glycerol dinitrate in the blood plasma of said subject in the range of 0.4 ng/mL to 2.0 ng/mL. In some embodiments, a single instance of topical administration of a composition of the present disclosure results in a peak concentration of 1,3 glycerol dinitrate in the blood plasma of said subject in the range of 0.4 ng/mL to 2.0 ng/mL.

There is also provided herein a method of treatment of animal subjects, for example, canine, feline, or equine subjects. In some embodiments, there is provided a method of treating equine laminitis in an equine subject comprising application of the compositions of the present disclosure.

NON-LIMITING EMBODIMENTS

The present disclosure is also described by way of the following non-limiting embodiment. However, the use of these and other embodiments anywhere in the specification is illustrative only and in no way limits the scope and meaning of the disclosure. Likewise, the disclosure is not limited to any particular preferred embodiment or aspect described herein. Indeed, modifications and variations may be apparent to those skilled in the art upon reading this specification, and such variations can be made without departing from the disclosure in spirit or in scope.

1. A pharmaceutically-acceptable topical composition comprising nitroglycerin that is essentially free of both water and hydrocarbon.
2. A pharmaceutically-acceptable topical composition comprising at least 4% weight by weight of nitroglycerin that is essentially free of both water and hydrocarbon.
3. The topical compositions of Embodiments 1 or 2 wherein the nitroglycerin is homogeneously distributed throughout said composition.
4. The topical compositions of any of Embodiments 1 through 3 further comprising at least 50% weight by weight of propylene glycol.

5. A pharmaceutically-acceptable topical composition that is essentially free of water and hydrocarbon and which comprises at least 5% weight by weight of nitroglycerin, and at least 50% weight by weight of propylene glycol.
6. The pharmaceutically-acceptable topical compositions of Embodiment 5 wherein the nitroglycerin is homogeneously distributed throughout said composition.
7. The topical composition of any of Embodiments 1 to 6 wherein said composition further comprises a viscosity-modifying agent selected from hydroxypropyl cellulose, polyoxyethylene sorbitan monooleate, acrylamide/sodium acryloyldimethyl taurate copolymer, SEPINEO P600 or a mixture thereof.
8. The topical composition of any of Embodiments 1 through 7 further comprising a fatty acid.
9. The topical composition of Embodiment 8 wherein said fatty acid is oleic acid or isostearic acid.
10. The topical composition of any of Embodiments 1 through 9 further comprising an emollient.
11. The topical composition of Embodiment 10 wherein said emollient comprises a fatty acid ester of an alpha hydroxy acid.
12. The topical composition of Embodiment 11 wherein said fatty acid ester of an alpha hydroxy acid comprises a C12, C13, C14 or C15 alkyl ester of lactic acid, Ceraphyl 41, or a mixture thereof
13. The topical composition of any of Embodiments 1 through 12 further comprising a lubricity-enhancing agent.
14. The topical composition of Embodiment 13 wherein said lubricity-enhancing agent is a silicone.
15. The topical composition of any of Embodiments 1 through 13 further comprising an antioxidant.
16. The topical composition of Embodiment 15 wherein said antioxidant is butylated hydroxytoluene.
17. A pharmaceutically-acceptable topical composition that is essentially free of water and hydrocarbon comprising at least 7% weight by weight of nitroglycerin, at least 70% weight by weight of propylene glycol, at least 8% oleic acid, about 1.5% Ceraphyl 41, and about 3% of hydroxypropyl cellulose.
18. A pharmaceutically-acceptable topical composition comprising at least 3% weight by weight of nitroglycerin that is essentially free of water, hydrocarbon and ethanol.
19. A pharmaceutically-acceptable topical composition that is essentially free of water and hydrocarbon comprising at least 3% weight by weight of nitroglycerin and in which nitroglycerin degrades by less than 5% when stored at 25° C. for six months.
20. A topical composition of any of Embodiments 1 through 19 further comprising an agent which indicates to which area of skin said topical composition has been applied.
21. The topical composition of Embodiment 20 in which said agent comprises a colorant.
22. A pharmaceutically-acceptable topical composition comprising:
    (i) about 0.5 to 10% w/w of an active agent;
    (ii) at least about 50% w/w of a diluent;
    (iii) about 1 to 15% w/w of a fatty acid;
    (iv) about 0.5 to 5% w/w of an emollient;
    (v) about 0.1 to 5% w/w a lubricity-enhancing agent;
    (vi) about 0.5 to 10% w/w viscosity-modifying agent; and
    (vii) optionally about 0.25 to 15% w/w of a molecular penetration enhancer (MPE).
23. The pharmaceutically-acceptable topical composition of Embodiment 22, wherein:
    (i) the active agent is selected from nitroglycerin (GTN), pentaerythritol tetranitrate (PETN), isosorbide dinitrate (ISDN), isosorbide mononitrate (ISMN), or a 1,2-dialkoxy-2-propyl nitrate, or a mixture thereof,
    (ii) the diluent is selected from the group comprising alcohols, medium chain triglycerides, Miglyol 812, a mixture of caprylic triglyceride and capric triglyceride, or propylene glycol;
    (iii) the fatty acid is selected from oleic acid or isostearic acid;
    (iv) the emollient is a fatty acid ester of an alpha hydroxy acid comprising a C12, C13, C14 or C15 alkyl ester of lactic acid, or a mixture of such alkyl esters;
    (v) the lubricity-enhancing agent is selected from a silicone or cyclic siloxane;
    (vi) the viscosity-modifying agent is selected from hydroxypropyl cellulose, polyoxyethylene sorbitan monooleate, acrylamide/sodium acryloyldimethyl taurate copolymer or a mixture thereof; and
    (viii) the MPE is selected from Brij L4, isopropyl myristate, isopropyl palmitate, dimethyl isosorbide, di(ethylene glycol) ethyl ether or a mixture thereof.
24. A pharmaceutically-acceptable topical composition comprising:
    (i) about 0.5 to 10% w/w nitroglycerin;
    (ii) at least 50% w/w propylene glycol;
    (iii) about 1 to 15% w/w oleic acid or isostearic acid;
    (iv) about 0.5 to 5% w/w Ceraphyl 41;
    (v) about 0.1 to 5% w/w cyclomethicone;
    (vi) about 0.5 to 10% w/w hydroxypropyl cellulose or SEPINEO P 600; and
    (vii) optionally about 0.25 to 15% w/w Brij L4, isopropyl myristate, dimethyl isosorbide, di(ethylene glycol) ethyl ether or a mixture thereof.
25. A method of manufacturing a pharmaceutically-acceptable topical composition according to any of Embodiments 1 through 24 comprising: (i) providing appropriate amounts of all excipients other than diluent and viscosity-modifying agent into a vessel, (ii) providing the appropriate amount of active agent combined, where required by the composition, with diluent, into said vessel (iii) agitating the mixture in said vessel until homogeneous, (iv) providing into said vessel the appropriate quantity of viscosity-modifying agent, and (v) mixing the combination thoroughly.
26. A method for treating a condition in a subject in which peripheral blood flow is compromised comprising topical administration of a formulation composition as provided in any of Embodiments 1 through 24.
27. The method of Embodiment 27 wherein said condition is a chronic tendinopathy, mastectomy skin flap necrosis, autonomic dysreflexia associated with spinal cord injury, intraoperative microsurgical vasospasm, chondrodermatitis nodularis helicis, chronic anal fissure, introital dyspareunia, vulvar pain associated with vulvodynia, or Raynaud's phenomenon.
28. The method of Embodiment 27 wherein said condition is selected from the group consisting of peripheral artery disease, peripheral vascular disease, diabetic neuropathy, tendinopathy, erectile dysfunction, alopecia, male pattern baldness and female pattern baldness.

29. The method of Embodiment 27 wherein said condition is associated with secondary Raynaud's phenomenon associated with one or more of: systemic sclerosis, CREST syndrome, systemic lupus erythematosus, rheumatoid disease, rheumatoid arthritis, Sjogren's syndrome, or polymyositis.
30. A method for ameliorating a symptom associated with compromised peripheral blood flow in a subject comprising topical administration of a formulation composition as provided in any of Embodiments 1 through 24.
31. The method of Embodiment 30 wherein said symptom comprises skin redness, cyanosis of the skin, skin blanching, low skin temperature, pain in the hands or feet, numbness in the hands or feet, tingling in the hands or feet, paresthesia, throbbing in the hands or feet, or the number of Raynaud's attacks in the hands or feet.
32. A method for radial artery vasodilation prior to cannulation comprising topical administration of a formulation composition as provided in any of Embodiments 1 through 24.
33. The method of any of Embodiments 27 through 0 wherein said subject has a likelihood or severity of headache that is reduced relative to that which accompanies application to the skin of said subject of 2% nitroglycerin ointment USP according to the label directions for the treatment of angina pectoris.
34. A method for treating or ameliorating Raynaud's phenomenon in a subject comprising application to the skin of the fingers of said subject a formulation composition consisting of a pharmaceutically acceptable topical formulation of nitroglycerin that is essentially free of both water and hydrocarbon wherein the viscosity of said formulation is less than 10,000 centipoise.
35. The method of any of Embodiments 27 through 34 wherein said formulation composition is applied to the subject at a dose per unit area of skin of no more than 9 mg cm$^{-2}$.
36. The method of any of Embodiments 27 through 35 wherein no more than 500 μL of said formulation composition is applied to a hand of the subject and said applied volume is sufficient to treat said condition or to ameliorate said symptom.
37. The method of any of Embodiments 27 through 36 wherein said formulation composition is applied to the subject once per day, twice per day, thrice per day or on an as needed basis.
38. The method of Embodiment 37 wherein said formulation composition is applied once per day in the morning.
39. The method of Embodiment 37 wherein the last application of said formulation composition in a day is at least two, three, four, five or six hours before said subject's bedtime.
40. The method of any of Embodiments 37, 38 and 39, wherein the recommended timing of said administration is indicated to said subject by a device worn by said subject.
41. The method of any of Embodiments 27 through 40 wherein said formulation composition causes a warming sensation that is no more than that of water when both said formulation composition and water are applied to the opposite hands of said subject at the same finite dose and the temperature of said formulation composition and water are both similar and in the range 23-28° C. and the cooling sensation is evaluated by said subject over a period of 5 minutes immediately following said application in a room with ambient temperature in the range 22-28° C. with a relative humidity in the range 40-70%.
42. The method of any of Embodiments 27 through 40 wherein said formulation composition causes a cooling sensation that is no more than that of water when both said formulation composition and water are applied to the opposite hands of said subject at the same finite dose and the temperature of said formulation composition and water are both similar and in the range 23-28° C. and the cooling sensation is evaluated by said subject over a period of 5 minutes immediately following said application in a room with ambient temperature in the range 22-28° C. with a relative humidity in the range 40-70%.
43. The method of Embodiments 27 through 40 wherein said treatment or amelioration is evidenced in a randomized placebo-controlled clinical study.
44. The method of any of Embodiments 27 through 40 wherein said treatment or amelioration is realized without a requirement for one or more of: (i) said formulation composition coming into contact with the skin of the second hand following administration to the first hand; (ii) rubbing said formulation composition into the skin; (iii) spreading said formulation composition by other than the container in which said formulation composition is provided.
45. The method of Embodiment 27 wherein said subject evidences in a controlled study an ability to hold the hand to which said formulation composition is applied in ice water for a period that is at least 50% longer after said administration than prior to said administration.
46. A method of treating a subject suffering from Raynaud's phenomenon comprising provision to said subject of a composition according to any of Embodiments 1 through 24 together with instructions advising that the amount of said formulation composition applied to a hand is to be adjusted based on the size of the hand.
47. A method of treating a subject suffering from Raynaud's phenomenon comprising provision to said subject of a formulation composition according to any of Embodiments 1 through 24 together with instructions advising that said formulation composition is not to be transported by air.
48. The method of any of Embodiments 27 through 40 wherein when said formulation composition is applied to a hand of said subject and when said subject handwrites on paper with said hand in an uncovered state 20 minutes following said formulation composition, no transference of remnant formulation composition is visible on said paper.
49. The method of any of Embodiments 27 through 40 wherein a single instance of said topical administration results in a peak concentration of nitroglycerin in the blood plasma of said subject no greater than realized following administration of 2% nitroglycerin ointment USP according to the label directions for the treatment of angina pectoris.
50. The method of any of Embodiments 27 through 40 wherein a single instance of said topical administration results in a peak concentration of 1,2 glycerol dinitrate in the blood plasma of said subject in the range of 0.4 ng/mL to 2.0 ng/mL.
51. The method of any of Embodiments 27 through 40 wherein a single instance of said topical administration results in a peak concentration of 1,3 glycerol dinitrate in the blood plasma of said subject in the range of 0.4 ng/mL to 2.0 ng/mL.

52. A method for treating equine laminitis in an equine subject comprising topical administration of a formulation composition as provided in any of Embodiments 1 through 24.

53. A kit for provision to a subject suffering from Raynaud's phenomenon comprising a composition according to any of Embodiments 1 through 24 together with instructions as to how much of said topical formulation of nitroglycerin is to be administered according to the hand size of said subject.

54. A formulation composition as provided in any of Embodiments 1 through 24, wherein the formulation is not incorporated or impregnated into a skin-contacting support member.

55. A formulation composition as provided in any of Embodiments 1 through 24 wherein said composition is incorporated or impregnated into a skin-contacting supporting member.

NON-LIMITING EXAMPLES

The present disclosure is also described and demonstrated by way of the following non-limiting examples. However, the use of these and other examples anywhere in the specification is illustrative only and in no way limits the scope and meaning of the disclosure or of any exemplified term. Likewise, the disclosure is not limited to any particular preferred embodiment or aspect described herein. Indeed, suitable modifications and variations may be apparent to those skilled in the art upon reading this specification, and such variations can be made without departing from the disclosure in spirit or in scope.

Example 1. Preparation and Assessment of Formulations with Different Gellants

Formulations of compositions as provided in Table 1 were prepared using the general procedure described under Example 11. These compositions reveal which of the selected set of excipients can be combined with 10% GTN Solution in PG to produce single phase viscous solutions. As provided in Table 1, combining 10% w/w of isopropyl palmitate, Crodamol GTCC or PPG-15 Stearyl Ether, 5% w/w BrijO20 or Brij S20, 3% w/w Capmul GMO, or 1% w/w Cyclomethicone 5-NF with 10% GTN Solution in PG yields cloudy solutions, indicating incomplete miscibilities. One day following the addition of 50 µL SEPINEO P 600 to 1 g of formulation, in each of the cases of 10% w/w DMSO, 10% w/w Oleic acid, 10% w/w Isostearic acid and 5% w/w Brij L4 combined with 10% GTN Solution in PG, transparent gels result.

TABLE 1

Topical formulation compositions prepared to assess the physical compatibilities of various excipients and the effects of addition of 50uL SEPINEO P 600 to 1g of formulation (Cl = Cloudy (where not indicated, formulations were transparent); Mky = Milky; Tlt = Translucent; Tsp = Transparent)

| | Formulation name | | | | | | | | | | | | | | | | | |
|---|---|---|---|---|---|---|---|---|---|---|---|---|---|---|---|---|---|---|
| | F64 | F65 | F66 | F67 | F68 | F69 | F70 | F71 | F72 | F73 | F74 | F75 | F76 | F77 | F78 | F79 | F80 | F80 |
| [wt % Nitroglycerin] | 9 | 9 | 9 | 9 | 9 | 9 | 9 | 9 | 9 | 9 | 9 | 9 | 10 | 10 | 10 | 10 | 10 | 10 |
| 10% GTN Solution in PG | 90 | 90 | 90 | 90 | 90 | 90 | 90 | 90 | 90 | 90 | 90 | 90 | 95 | 95 | 95 | 97 | 99 | 95 |
| Isopropyl palmitate | 10 | | | | | | | | | | | | | | | | | |
| Crodamol GTCC | | 10 | | | | | | | | | | | | | | | | |
| Isopropyl myristate | | | 10 | | | | | | | | | | | | | | | |
| Oleyl alcohol | | | | 10 | | | | | | | | | | | | | | |
| Dimethyl isosorbide | | | | | 10 | | | | | | | | | | | | | |
| Transcutol | | | | | | 10 | | | | | | | | | | | | |
| DMSO | | | | | | | 10 | | | | | | | | | | | |
| Oleic acid | | | | | | | | 10 | | | | | | | | | | |
| Diisopropyl adipate | | | | | | | | | 10 | | | | | | | | | |
| Isostearic acid | | | | | | | | | | 10 | | | | | | | | |
| PPG-15 Stearyl Ether | | | | | | | | | | | 10 | | | | | | | |
| Dimethyl isosorbide | | | | | | | | | | | | 10 | | | | | | |
| Ceraphyl 41 | | | | | | | | | | | | | 5 | | | | | |
| BrijO20 | | | | | | | | | | | | | | 5 | | | | |
| Brij L4 | | | | | | | | | | | | | | | 5 | | | |
| Capmul GMO | | | | | | | | | | | | | | | | 3 | | |
| Cyclomethicone 5-NF | | | | | | | | | | | | | | | | | 1 | |
| Brij S20 | | | | | | | | | | | | | | | | | | 5 |
| Prior to addition | Cl | Cl | | | | | | | | | Cl | | Cl | | Cl | Cl | Cl | Cl |
| Post addition | Cl | Cl | Cl | Cl | Cl | Cl | Cl | Cl | Cl | Cl | Cl | Cl | Cl | Cl | Cl | Cl | Cl | Cl |
| 24 h post addition | C | Mky | Tlt | Mky | Tlt | Tlt | Tsp | Tsp | Tlt | Tsp | Mky | Tlt | Tlt | Mky | Tsp | Mky | Mky | Mky |

Example 2. Preparation and Assessment of Formulations with Different Gellants Formulations of compositions as provided in were prepared using the general procedure described under Example 11. As the formulations would be assessed in a study with human volunteers, the compositions were prepared as placebos, that is using pure propylene glycol in place of a solution of GTN in propylene glycol. As provided in Table 2, it proved to not be possible to produce gels according to the standard procedure described under Example 11 for each of the alternative gellants Ceraphyl 41, Methocel E4M, Natrosol 250HHR, Carbopol 980, Carbopol 5984, Compritol 888, Polyethylene Glycol 1450 and Kollidon CL-M. Only SEPINEO P 600 and HPC (HY119) yielded clear, stable gels.

TABLE 2

Topical formulation compositions prepared to assess the effects of various gellants. All amounts are given in % w/w.

| Ingredients | F86-P | F90-P | F91-P | F92-P | F93-P | F94-P | F95-P | F95-P | F96-P |
|---|---|---|---|---|---|---|---|---|---|
| Propylene glycol | 80.00 | 82.00 | 82.00 | 82.00 | 82.00 | 82.00 | 82.00 | 82.00 | 82.00 |
| Oleic acid | 13.00 | 13.00 | 13.00 | 13.00 | 13.00 | 13.00 | 13.00 | 13.00 | 13.00 |
| Isostearic acid | | | | | | | | | |
| Ceraphyl 41 | 2.00 | 2.00 | 2.00 | 2.00 | 2.00 | 2.00 | 2.00 | 2.00 | 2.00 |
| SEPINEO P 600 | 5.00 | | | | | | | | |
| Methocel E4M | | 3.00 | | | | | | | |
| HPC (HY119) | | | 3.00 | | | | | | |
| Natrosol 250HHR | | | | 3.00 | | | | | |
| Carbopol 980 | | | | | 3.00 | | | | |
| Carbopol 5984 | | | | | | 3.00 | | | |
| Compritol 888 | | | | | | | 3.00 | | |
| Polyethylene Glycol 1450 | | | | | | | | 3.00 | |
| Kollidon CL-M | | | | | | | | | 3.00 |
| Observation | Clear gel | failed | Clear gel | failed | failed | failed | failed | failed | failed |

Example 3. Esthetics Assessments of Formulations with Different Gellants

Formulations of compositions as provided in Table 3 were prepared using the general procedure described under Example 11. As the formulations would be assessed in a study with human volunteers, the compositions were prepared as placebos, that is using pure propylene glycol in place of a solution of GTN in propylene glycol. Each formulation was assessed by each of four volunteers according to the procedure provided under Example 15. As provided in Table 4, the tested compositions score better than acceptably well in terms of their esthetic characteristics.

TABLE 3

Topical formulation compositions prepared for evaluation of esthetic characteristics.

| 10% Nitroglycerin in PG | F98 - Placebo | F99 - Placebo | F100 - Placebo |
|---|---|---|---|
| Propylene glycol | 82.50 | 82.50 | 86.50 |
| Oleic acid | 12.00 | 12.00 | 12.00 |
| Ceraphyl 41 | 1.50 | 1.50 | 1.50 |
| SEPINEO P 600 | 4.00 | | |
| HPC (HY119) | | 4.00 | |

TABLE 4

Results of the esthetic evaluation of formulations provided in Table 3 by four volunteers. Each attribute was ranked on a zero to 4 scale, so the maximum score for each attribute is 4.

| Esthetic Attribute: | F98PLCB | F99PLCB | F100PLCB |
|---|---|---|---|
| Thickness/viscosity | 2.9 | 2.9 | 2.6 |
| Consistency | 3.8 | 3.8 | 4.0 |
| Spreadability | 3.8 | 3.8 | 4.0 |
| Absorbency | 3.5 | 3.0 | 3.8 |
| After feel & Appearance - Immediate | 3.0 | 2.6 | 3.3 |
| After feel & Appearance - Delayed | 3.4 | 2.8 | 3.6 |
| Tolerability | 4.0 | 4.0 | 4.0 |
| Odor | 3.3 | 3.3 | 3.7 |

Example 4. Preparation and Assessment of Topical Formulations with Different Compositions Formulations of compositions as provided in Table 5 were prepared using the general procedure described under Example 11. The amounts of GTN, combined with its degradants, that have permeated through split-thickness human cadaver skin at 2, 4, 6 and 24 hours following formulation application as measured, using a radiolabel counting assay, according to the procedure described under Example 12 are provided (referenced to 2% USP GTN ointment) in FIG. 1, expressed in µg per $cm^{-2}$ of application area.

TABLE 5

Topical nitroglycerin formulation compositions. All amounts are given in % w/w. Nitroglycerin is introduced as a 10% w/w solution in propylene glycol (PG), the amount of which solution is provided (for clarity, the % w/w amount of nitroglycerin provided by such introduction is also listed, in brackets)

| | 2% | Formulation name | | | | | |
|---|---|---|---|---|---|---|---|
| | USP | F46 | F47 | F48 | F49 | F50 | F51 |
| [wt % Nitroglycerin] | 2 | 2 | 2 | 2 | 2 | 2 | 2 |
| 10% GTN Solution in PG | | 20 | 20 | 20 | 20 | 20 | 20 |

TABLE 5-continued

Topical nitroglycerin formulation compositions. All amounts are given in % w/w. Nitroglycerin is introduced as a 10% w/w solution in propylene glycol (PG), the amount of which solution is provided (for clarity, the % w/w amount of nitroglycerin provided by such introduction is also listed, in brackets)

| | 2% | Formulation name | | | | | |
|---|---|---|---|---|---|---|---|
| | USP | F46 | F47 | F48 | F49 | F50 | F51 |
| DMSO | | | | | 35 | 21 | 18 |
| Propylene glycol | | | | | | | |
| Ethanol | | | | | 16 | | |
| Water | | | | | | 50 | |
| Brij L4 | | | | | 4 | 5 | |
| Lauryl lactate | | | | | 3 | 2 | |
| Crodamol GTCC | | | | | 20 | | |
| Glycerin | | | | | | | 10 |
| Transcutol P | | | | | | | 35 |
| IPA | | | | | | | 10 |
| Polyglyceryl-3-dioleate NF | | | | | | | 5 |
| HY119 | | | | | 2 | 2 | 2 |
| Cetostearyl Alcohol | | 8 | 8 | 8 | | | |
| Ceteth 2 | | 0.97 | | | | | |
| Ceteth 20 | | 5.03 | | | | | |
| Oleth-10 | | | 1.97 | | | | |
| Oleth-20 | | | 4.03 | | | | |
| Steareth-10 | | | | 1.2 | | | |
| Steareth-20 | | | | 4.8 | | | |
| Oleic acid | | 15 | | 10 | | | |
| Isostearyl alcohol | | | 15 | 10 | | | |
| Isopropyl palmitate | | 7 | 7 | 7 | | | |
| Water | | 64 | 64 | 59 | | | |

Figure 2:
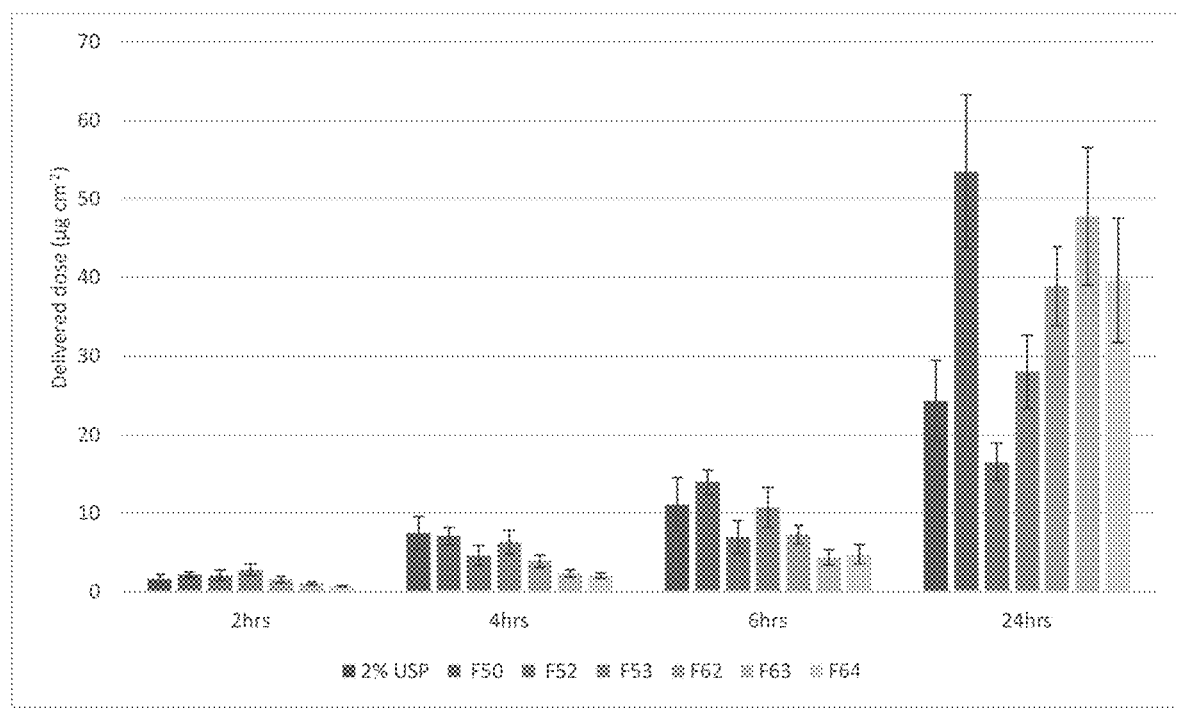
FIG. 2 illustrates the amounts of GTN, combined with its degradants, that have permeated through split-thickness human cadaver skin at 2, 4, 6 and 24 hours following application of each of the topical GTN formulations detailed in Table 6, as described in Example 5 provided herein.

Example 5. Preparation and Assessment of Topical Formulations with Different Compositions Formulations of compositions as provided in Table 6 were prepared using the general procedure described under Example 11. The amounts of GTN, combined with its degradants, that have permeated through split-thickness human cadaver skin at 2, 4, 6 and 24 hours following formulation application as measured, using a radiolabel counting assay, according to the procedure described under Example 12 are provided (referenced to 2% USP GTN ointment) in FIG. 2, expressed in µg per $cm^{-2}$ of application area.

TABLE 6

Topical nitroglycerin formulation compositions. All amounts are given in % w/w. Nitroglycerin is introduced as a 10% w/w solution in propylene glycol (PG), the amount of which solution is provided (for clarity, the % w/w amount of nitroglycerin provided by such introduction is also listed, in brackets)

| | 2% | Formulation name | | | | | |
|---|---|---|---|---|---|---|---|
| | USP | F50 | F52 | F53 | F62 | F63 | F64 |
| [wt % Nitroglycerin] | 2 | 2 | 2 | 2 | 2 | 2 | 2 |
| 10% GTN Solution in PG | | 20 | 30 | 30 | 28.61 | 28.34 | 35 |
| DMSO | | 21 | | | 38.15 | 37.79 | 35 |
| Water | | 50 | 33 | 40 | 23.84 | 23.62 | 20 |
| Brij L4 | | 5 | | | | | |
| Lauryl lactate | | 2 | | | | | |
| Kolliphor PS 20 | | | | | | | |
| Kolliphor SLS | | | | | | | |
| Glycerin | | | | | | | |
| Cyclomethicone | | | | | | | |
| HPC (HY119) | | 2 | | | | | 2 |
| Carbopol 980 | | | | | 1.53 | 1.51 | |
| Ammonia | | | | | 0.24 | 0.24 | |
| Cetostearyl alcohol | | | 8 | 8 | | | |
| Petrolatum | | | | 4 | | | |
| Steareth-10 | | | 2.59 | 5.08 | | | |
| Steareth-20 | | | 5.41 | 2.92 | | | |
| Lauroglycol FCC | | | | 5 | | | |
| Polyglyceryl 3 dioleate | | | | 3 | | | |
| Capryol 90 | | | | 2 | | | |
| Oleic acid | | | 7 | | | | |
| Isostearyl alcohol | | | 7 | | | | |
| Isopropyl palmitate | | | 7 | | | | |
| BrijS20 | | | | | 4.77 | 4.72 | 5 |
| Dimethyl isosorbide | | | | | 2.86 | 2.83 | 3 |
| Sodium lauryl sulfate | | | | | | 0.94 | |

Figure 3:
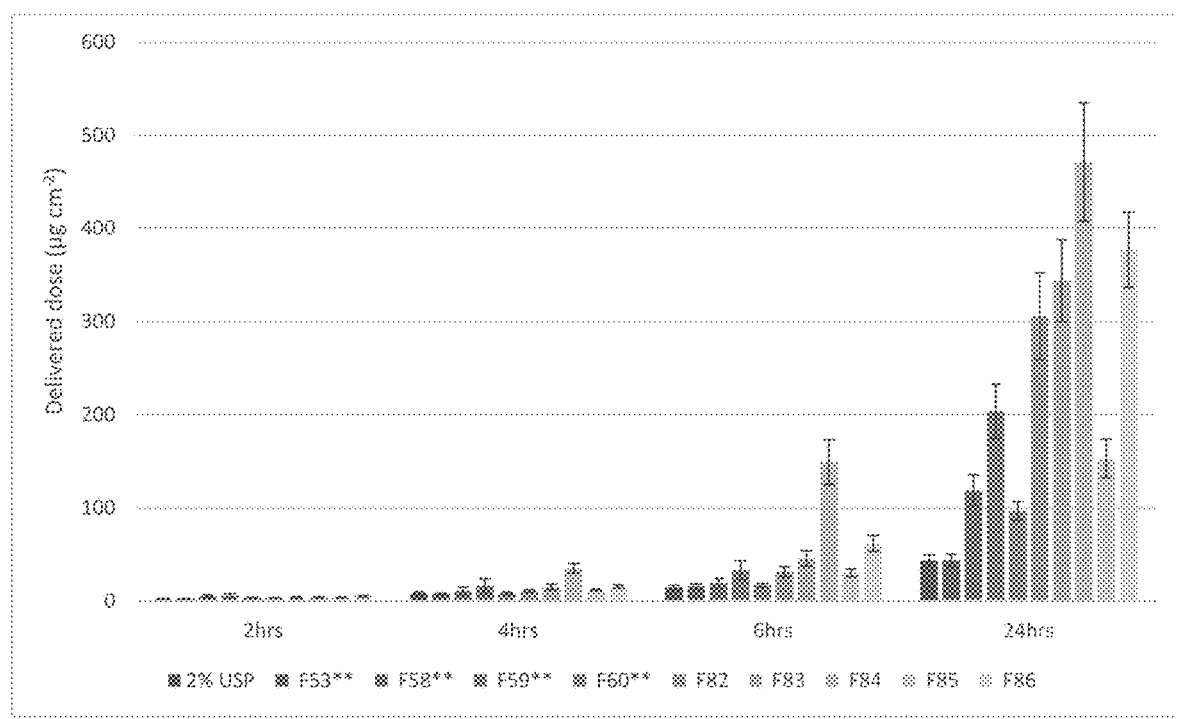
FIG. 3 illustrates the amounts of GTN, combined with its degradants, that have permeated through split-thickness human cadaver skin at 2, 4, 6 and 24 hours following application of each of the topical GTN formulations detailed in Table 7, as described in Example 6 provided herein.

Example 6. Preparation and Assessment of Topical Formulations with Different Compositions Formulations of compositions as provided in Table 7 were prepared using the general procedure described under Example 11. The amounts of GTN, combined with its degradants, that have permeated through split-thickness human cadaver skin at 2, 4, 6 and 24 hours following formulation application as measured, using a radiolabel counting assay, according to the procedure described under Example 12 are provided (referenced to 2% USP GTN ointment) in FIG. 3, expressed in µg per $cm^{-2}$ of application area.

TABLE 7

Topical nitroglycerin formulation compositions. All amounts are given in % w/w. Nitroglycerin is introduced as a 10% w/w solution in propylene glycol (PG), the amount of which solution is provided (for clarity, the % w/w amount of nitroglycerin provided by such introduction is also listed, in brackets)

| | 2% USP | F53** | F58** | F59** | F60** | F82 | F83 | F84 | F85 | F86 |
|---|---|---|---|---|---|---|---|---|---|---|
| [wt % Nitroglycerin] | 2 | 3 | 5 | 5 | 5 | 9.5 | 8 | 8 | 8 | 8 |
| 10% GTN Solution in PG | | 30 | 50 | 50 | 50 | 95 | 80 | 80 | 80 | 80 |
| Cetostearyl Alcohol | | 8 | | | 6 | | | | | |
| Petrolatum | | 4 | | | | | | | | |
| Stereth-10 | | 5.08 | | | | | | | | |
| Stereth-20 | | 2.92 | | | | | | | | |
| Lauroglycol FCC | | 5 | | | | | | | | |
| Polyglyceryl 3 dioleate | | 3 | | | | | | | | |
| Capryol 90 | | 2 | | | | | | | | |
| Water | | 40 | | | 21 | | | | | |
| Cyclomethicone | | | 5 | | | | | | | |
| PEG300 | | | 5 | | | | | | | |
| Dipropylene glycol | | | 5 | | | | | | | |
| GMS | | | 20 | | | | | | | |
| Mineral oil | | | | 10 | | | | | | |
| Arlacel 165 | | | 0.6 | 3 | | | | | | |
| GMIS | | | 14.4 | 12 | | | | | | |
| Geleol mono DI NF | | | | | 25 | | | | | |
| Kolliphor EL | | | | | 4 | | | | | |
| Kolliphor RH 40 | | | | | 4 | | | | | |
| Crodamol GTCC | | | | | 15 | | | | | |
| DMSO | | | | | | 6 | | | | |
| Oleic acid | | | | | | | 13 | | | |
| Diisopropyl adipate | | | | | | | | 13 | | |
| Isostearic acid | | | | | | | | | | 13 |
| Dimethyl Isosorbide | | | | | | 6 | | | | |
| Ceraphyl 41 | | | | | | | | 2 | 2 | 2 |
| Brij L4 | | | | | | | 3 | | | |
| SEPINEO P 600 | | | | | | 5 | 5 | 5 | 5 | 5 |

Figure 4:
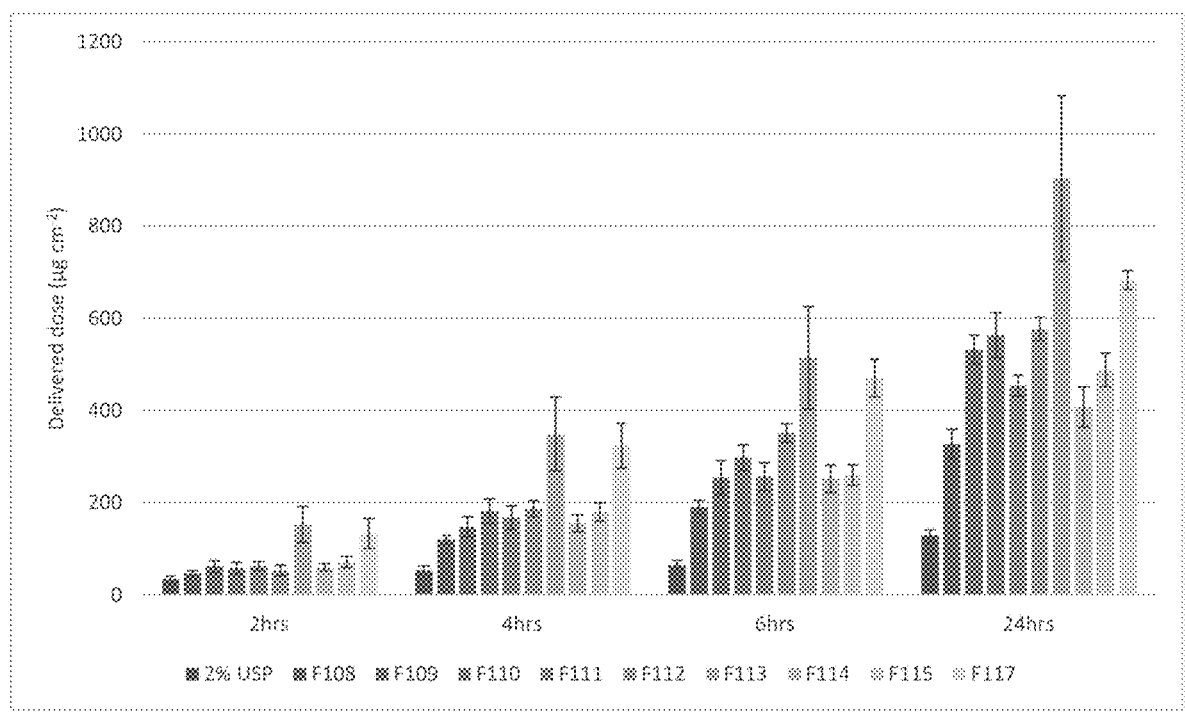
FIG. 4 illustrates the amounts of GTN, combined with its degradants, that have permeated through split-thickness human cadaver skin at 2, 4, 6 and 24 hours following application of each of the topical GTN formulations detailed in Table 8, as described in Example 7 provided herein.

Example 7. Preparation and Assessment of Topical Formulations with Different Compositions Formulations of compositions as provided in Table 8 were prepared using the general procedure described under Example 11. The amounts of GTN, combined with its degradants, that have permeated through split-thickness human cadaver skin at 2, 4, 6 and 24 hours following formulation application as measured, using a radiolabel counting assay, according to the procedure described under Example 12 are provided (referenced to 2% USP GTN ointment) in FIG. 4, expressed in µg per $cm^{-2}$ of application area.

TABLE 8

Topical nitroglycerin formulation compositions. All amounts are given in % w/w. Nitroglycerin is introduced as a 10% w/w solution in propylene glycol (PG), the amount of which solution is provided (for clarity, the % w/w amount of nitroglycerin provided by such introduction is also listed, in brackets)

| | 2% USP | F108 | F109 | F110 | F111 | F112 | F113 | F114 | F115 | F117 |
|---|---|---|---|---|---|---|---|---|---|---|
| [wt % Nitroglycerin] | 2 | 8.2 | 8.3 | 8.4 | 8.5 | 8.15 | 8.6 | 8.6 | 8.7 | 8.6 |
| 10% GTN Solution in PG | | 82 | 83 | 84 | 85 | 81.5 | 86 | 86 | 87 | 86 |
| Oleic acid | | 12 | 12 | | | 12 | | | | |
| Isostearic acid | | | | 10 | 10 | | | | | |
| Ceraphyl 41 | | 1.5 | 1.5 | 1.5 | 1.5 | | | | | |
| Cyclomethicone 5 | | 0.5 | 0.5 | 0.5 | 0.5 | 0.5 | | | | |
| HPC (HY119) | | | 3 | | 3 | | | | 3 | |
| SEPINEO P 600 | | 4 | | 4 | | 4 | 4 | 4 | | 4 |
| Brij L4 | | | | | | 2 | 2 | 2 | 2 | 2 |
| Isopropyl myristate | | | | | | | | 8 | | |
| Dimethyl isosorbide | | | | | | | | | 8 | 8 |
| Transcutol | | | | | | | | | | 8 |

Figure 5:
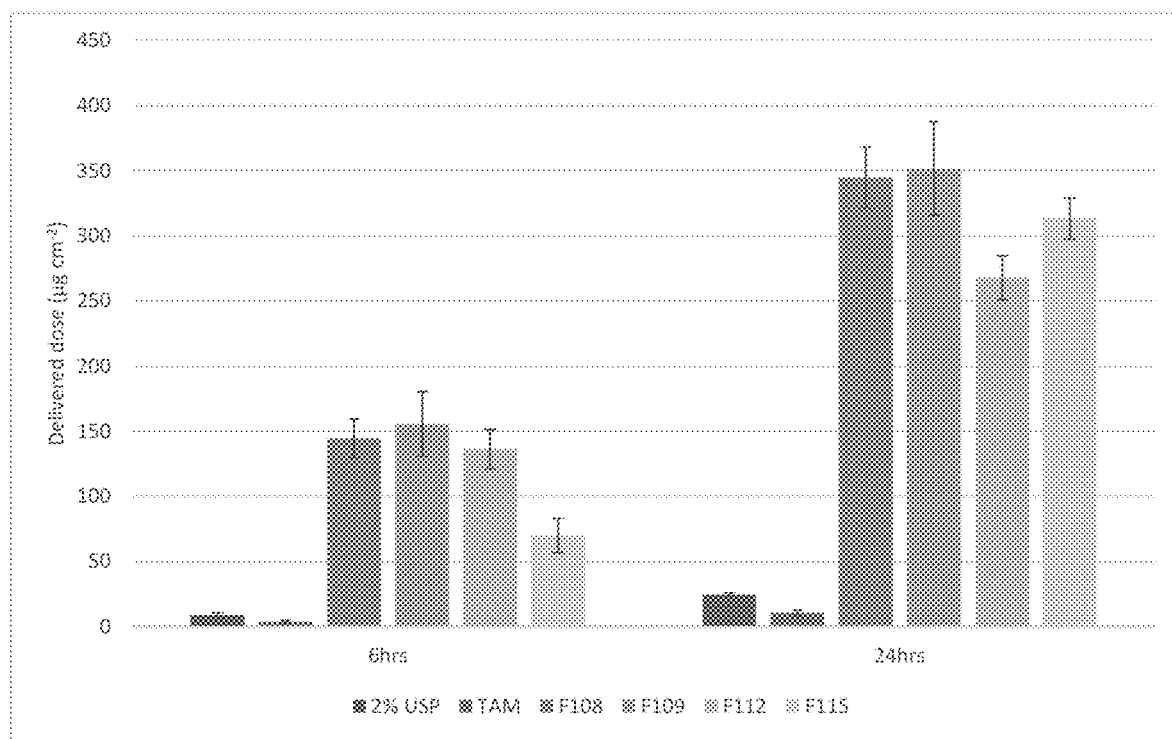
FIG. 5 illustrates the amounts of GTN, combined with its degradants, that have permeated through split-thickness human cadaver skin at 6 and 24 hours following application of each of the topical GTN formulations detailed in Table 9, as described in Example 7 provided herein (formulation TAM is also referred to as MQX-503).

Example 8. Preparation and Assessment of Topical Formulations with Different Compositions Formulations of compositions as provided in Table 9 were prepared using the general procedure described under Example 11. The amounts of GTN, combined with its degradants, that have permeated through split-thickness human cadaver skin at 6 and 24 hours following formulation application as measured, using a radiolabel counting assay, according to the procedure described under Example 12 are provided (referenced to 2% USP GTN ointment and MQX-503 also referred to as TAM) in FIG. 5, expressed in μg per cm$^{-2}$ of application area. MQX-503 is topical formulations of GTN which was investigated as a treatment of Raynaud's phenomenon (Chung L, et al. Arthritis Rheum. 2009 March; 60(3):870-7), but which was not approved by the US Food and Drug Administration (see https://invivo.pharmaintelligence.inform.com/SC030490/MediQuest-receives-FDA-response-for-Raynauds-drug)

TABLE 9

Topical nitroglycerin formulation compositions. All amounts are given in % w/w. Nitroglycerin is introduced as a 10% w/w solution in propylene glycol (PG), the amount of which solution is provided (for clarity, the % w/w amount of nitroglycerin provided by such introduction is also listed, in brackets)

| | 2% | | Formulation name | | | |
|---|---|---|---|---|---|---|
| | USP | TAM | F108 | F109 | F112 | F115 |
| [wt% Nitroglycerin] | 2 | 1 | 8.2 | 8.3 | 8.15 | 8.7 |
| 10% Nitroglycerin in PG | | | 82 | 83 | 81.5 | 87 |
| Oleic acid | | | 12 | 12 | 12 | |
| Isostearic acid | | | | | | |
| Ceraphyl 41 | | | 1.5 | 1.5 | | |
| Cyclomethicone 5-NF | | | 0.5 | 0.5 | 0.5 | |
| Hydroxypropyl cellulose (HY119) | | | | 3 | | 3 |
| Sepineo P600 | | | 4 | | 4 | |
| Brij L4 | | | | | 2 | 2 |
| Dimethyl isosorbide | | | | | | 8 |

Example 9. Preparation and Assessment of Topical Formulations with Different Compositions Formulations of compositions as provided in Table 10 were prepared using the general procedure described under Example 11. Stability for each of these formulations assessed according to the general procedure provided in Example 14 is provided in

TABLE 11

TABLE 10. Topical nitroglycerin formulation compositions. All amounts are given in % w/w. Nitroglycerin is introduced as a 10% w/w solution in propylene glycol (PG), the amount of which solution is provided (for clarity, the % w/w amount of nitroglycerin provided by such introduction is also listed, in brackets)

| Ingredients | F108 | F109 | F110 | F111 | F112 | F113 | F114 | F115 | F116 | F117 | F146 | F147 |
|---|---|---|---|---|---|---|---|---|---|---|---|---|
| [Nitroglycerin] | 8.2 | 8.3 | 8.4 | 8.5 | 8.15 | 8.6 | 8.6 | 8.7 | 8.8 | 8.6 | 8.25 | 8.65 |
| 10% Nitroglycerin in PG | 82 | 83 | 84 | 85 | 81.5 | 86 | 86 | 87 | 88 | 86 | 82.5 | 86.5 |
| Oleic acid | 12 | 12 | | | 12 | | | | | | 12.00 | |
| Isostearic acid | | | 10 | 10 | | | | | | | | 8.00 |
| Ceraphyl 41 | 1.5 | 1.5 | 1.5 | 1.5 | | | | | | | | |
| Cyclomethicone 5-NF | 0.5 | 0.5 | 0.5 | 0.5 | 0.5 | | | | | | 0.50 | 0.50 |
| Hydroxypropyl cellulose (HY119) | | 3 | | 3 | | | | 3 | | | 3.00 | 3.00 |
| SEPINEO P 600 | 4 | | 4 | | 4 | 4 | 4 | | 4 | 4 | | |
| Brij L4 | | | | | 2 | 2 | 2 | 2 | 2 | 2 | 2.00 | 2.00 |
| Isopropyl myristate | | | | | 8 | | | 6 | | | | |
| Dimethyl isosorbide | | | | | | 8 | 8 | | | | | |
| Transcutol | | | | | | | | 8 | | | | |
| | 100 | 100 | 100 | 100 | 100 | 100 | 100 | 100 | 100 | 100 | 100 | 100 |

TABLE 11

Chemical stability data for topical nitroglycerin formulation compositions. Potencies are expressed as percentages of the nitroglycerin assay at time zero (as provided in the first column).

| Formln | Average mg/g t = 0 | 1 month 25° C. % Potency | 1 month 40° C. % Potency | 3 month 25° C. % Potency | 3 month 40° C. % Potency | 6 month 25° C. % Potency | 6 month 40° C. % Potency |
|---|---|---|---|---|---|---|---|
| F108 | 74.24 | 102.0% | 96.8% | 104.5% | 97.6% | 99.8% | 91.9% |
| F109 | 75.48 | 97.3% | 99.7% | 101.4% | 95.5% | 98.1% | 84.9% |
| F110 | 76.92 | 100.0% | 97.7% | 101.5% | 95.3% | 98.3% | 83.8% |
| F111 | 78.49 | 97.7% | 95.7% | 99.2% | 93.4% | 97.3% | 84.1% |
| F112 | 74.61 | 101.1% | 98.5% | 103.5% | 95.5% | 98.4% | 84.8% |
| F114 | 81.26 | 98.4% | 92.0% | 93.3% | 80.1% | 92.5% | 71.9% |
| F115 | 77.74 | 102.5% | 96.8% | 98.2% | 88.9% | 103.1% | 81.9% |
| F117 | 77.15 | 101.4% | 94.8% | 96.2% | 82.0% | 96.7% | 76.9% |
| F146 | 74.16 | | | 98.5% | 94.5% | | |
| F147 | 78.57 | | | 103.1% | 100.6% | | |

Example 10. Preparation and Assessment of Topical Formulations with Different Compositions Formulations of compositions as provided in Table 12 were prepared using the general procedure described under Example 11. Stability for each of these formulations assessed according to the general procedure provided in Example 14 is provided in Table 13.

TABLE 12

Topical nitroglycerin formulation compositions. All amounts are given in % w/w. Nitroglycerin is introduced as a 10% w/w solution in propylene glycol (PG), the amount of which solution is provided (for clarity, the % w/w amount of nitroglycerin provided by such introduction is also listed, in brackets)

| Ingredients | F108 | F109 | F112 | F148 | F149 | F150 | F151 |
|---|---|---|---|---|---|---|---|
| [Nitroglycerin] | 8.2 | 8.3 | 8.15 | 10 | 8.13 | 8.15 | 8.15 |
| 10% Nitroglycerin in PG | 82 | 83 | 81.5 | 100 | 81.3 | 81.5 | 81.5 |
| Oleic acid | 12 | 12 | 12 | | 12 | | 10 |
| Ceraphyl 41 | 1.5 | 1.5 | | | | | |
| Cyclomethicone 5-NF | 0.5 | 0.5 | 0.5 | | 0.5 | 0.5 | 0.5 |
| Hydroxypropyl cellulose (HY119) | | 3 | | | | | |
| Sepineo P600 | 4 | | 4 | | 4 | 4 | 4 |
| Brij L4 | | | 2 | | 2 | 2 | 2 |
| Ethanol | | | | | | 12 | |
| BHT | | | | | 0.2 | | |
| Lactose anhydrous | | | | | | | 2 |
| | 100 | 100 | 100 | 100 | 100 | 100 | 100 |

TABLE 13

Chemical stability data for topical nitroglycerin formulation compositions. Potencies are expressed as percentages of the nitroglycerin assay at time zero.

| Formln | 1 month 25° C. % Potency | 1 month 40° C. % Potency | 2 month 25° C. % Potency | 2 month 40° C. % Potency | 3 month % Potency at 40° C. | 6 month % Potency at 40° C. |
|---|---|---|---|---|---|---|
| F108 | 101.5% | 99.1% | 98.7% | 96.5% | 92.5% | 88.3% |
| F109 | 98.9% | 99.9% | 99.4% | 97.5% | 93.9% | 88.7% |
| F112 | 102.8% | 100.6% | 100.9% | 96.9% | 93.8% | 87.5% |
| F148 | 101.0% | 98.9% | 101.8% | 96.6% | 93.5% | 88.6% |
| F149 | 101.4% | 101.8% | 99.7% | 100.7% | 95.6% | 100.7% |
| F150 | 99.6% | 99.6% | 98.0% | 97.3% | 91.6% | 79.0% |

Example 11. General Procedure for Formulation Preparation

The requisite amount of each excipient, other than gellant(s), required for the given formulation composition is provided by accurate volumetric or gravimetric means, as appropriate, into a suitable glass media bottle. The requisite amount of nitroglycerin as a 10% solution in propylene glycol is provided by accurate weighing and added to the glass media bottle. The media bottle is capped, and the contents sonicated at room temperature until the mixture is homogeneous. The gellants(s), if required for the given formulation composition, are then introduced into the homogeneous solution and the mixture sonicated until a homogeneous material of the desired viscosity is obtained.

Example 12. General Procedure for Skin Delivery and Permeation Measurement

Franz diffusion cell experiments were used to analyze the extent of delivery of nitroglycerin and of its potential degradation products from compositions taught under the present disclosure into and across human skin. Franz diffusion cells are a common and well-known method for measuring transdermal flux rates. The general Franz cell procedure is described by Franz.

In the present examples, Franz diffusion cells ("FDC"s) with a 3.3 mL receptor well volume were used with split thickness human cadaver skin (0.015"-0.018", from Allo-Source (Centennial, CO) or Skin Bank NY Firefighters (New York, NY). The donor well addresses a skin area of about 0.55 cm$^2$. The receptor wells were filled with phosphate buffered saline solution at pH 7.4 ("PBS") containing 0.01% sodium azide (a preservative) (the "Receptor Fluid"), this fluid having been verified as providing sink conditions for nitroglycerin throughout the experiments. The receptor wells of the FDCs were maintained at 32($\pm$1°) C in a stirring dry block with continual agitation of the Receptor Fluid in the receptor well using a magnetic stir bar. Under these conditions the exterior temperature of the skin is maintained at 30($\pm$1°) C Donor and receptor chambers were clamped about the skin piece under uniform pressure using a pinch clamp (SS #18 VWR 80073-350).

After the FDCs were assembled, the skin was allowed to hydrate for 20 minutes in contact with the receptor fluid. Any FDCs that evidenced any leakage during this period were discarded. The integrity and quality of each skin piece was tested prior to application of the test formulations through measurement of the transepidermal electrical resistance ("TEER"). Skin pieces evidencing an excessively low TEER signal were discarded and the TEER values of accepted skin pieces were used to guide the distribution of test formulation samples over the skin piece set.

Where analyses would be performed by radiolabel counting, 200 μL of test formulation was first spiked with 20 μL of glycerol [2-14C] trinitrate (nitroglycerin [2-14C]) dissolved in ethanol at a concentration of 0.1 mCi mL-1 (American Radiolabeled Chemicals, ARC 0714-50) and the formulation intimately remixed.

Except where otherwise noted, six replicates of each test formulation were examined, typically in a batch of some 36 FDCs in total. Each test formulation was applied at a finite dose of 5 μL (9 mg cm$^{-2}$). A sample (typically 300 ul) was abstracted from each receptor well at preset times, typically 2, 4, 6 and 24 h, the receptor well being replenished with fresh Receptor Fluid. The concentration of nitroglycerin in each receptor well sample was assayed by HPLC or LC-MS analytical method (e.g. Example 13) or by radiolabel counting. For radiolabel counting, each 300 μL sample was placed into a scintillation vial into which 600 μL of scintillation cocktail (PerkinElmer Ultima Gold XR from PerkinElmer, Santa Clara CA) is added. The samples were then analyzed using a liquid scintillation counter ("LSC"). When reporting the mass of the mass of the delivered dose in the receptor compartment, it was assumed that all radiolabeled permeants were present as GTN.

Except where otherwise noted, at the end of the experiment (typically 24 hours), residual formulation was removed from the skin exterior with a pipette. The FDC was disassembled, and the skin washed with 200 μL EtOH-Water 50-50 which was allowed to contact the skin exterior for 5 mins and then discarded and the skin exterior wiped dry with a KimWipe. The successive topmost layers of the stratum corneum were removed by three (3) times applying cellophane tape to the skin and then pulling off the tape. Tape strippings were discarded, the material present in those peripheral layers being considered absorbed only superficially. The epidermal and dermal layers were separated, using heating to 60° C. for no more than one minute if required. The epidermal and dermal sections were placed into 4 mL glass vials. 3 mL of water-ethanol 50:50 by volume was added to each vial and the vials agitated on an orbital shaker for 24 hours at 40° C. At the end of the extraction period, aliquots of the extraction solvent were drawn and analyzed by the verified HPLC or LC-MS method, or by radiolabel counting, as above.

Example 13. Analytical Methods for GTN and its Possible Degradants

To assay each of GTN, 1,3-DNG and 1,2-DNG, a high-performance liquid chromatography ("HPLC") method using ultraviolet ("UV") detection was implemented on an Agilent 1260 HPLC, using an Agilent Eclipse XDB-CN 2.1×150 mm, 5 μm column and detection at 215 nm. A 10 μL injection volume and a flow rate of 1.0 mL min$^{-1}$ were used. Mobile phases A and B were water and methanol, respectively, using a gradient of 0 min: 80% A; 1 min: 80% A; 5 min: 60% A; 7 min: 60% A and a post equilibrium time of 3 mins.

Example 14. General Procedure for Stability Study

For formulation stability studies, test formulations (typically 40 mL) were loaded into amber glass vials and stored in stability chambers operating at both 25° C. and 40° C. (the relative humidity was not recorded as the vials were sealed). Stability tests conducted at 40° C. represent 'accelerated conditions' and as a rule of thumb stability at 6 months under these conditions is expected to be similar to stability observed after 24 months of storage at 25° C. An aliquot from each test formulation sample (typically 30 or 40 μL) was abstracted at each predetermined time point (e.g. 0 and 2 weeks), weighed accurately, and diluted with 2 mL of ethanol. The mixture was then rotated in a glass vial on a rotisserie at room temperature until fully dissolved. Triplicate samples from each glass vial were then analyzed by the verified HPLC analytical method as provided under Example 13.

Example 15. General Procedure for Assessing Formulation Esthetics

To assess the esthetic characteristics of a given test formulation, the formulation is provided to each of a set of subjects, together with an instruction sheet and a scoring sheet. The instructions direct the subject to dispense a suitable dose of the test formulation onto a stipulated area of skin, to spread the applied formulation over a stipulated area, and to record stipulated sensations and observations. In a typical study, each subject is directed to use a provided plastic, disposable syringe with an approximately 60 μL capacity, to administer a 90 μL dose in approximately 5 equal aliquots of the test formulation, one to the back of each finger (and thumb) of one hand. A single finger of the other hand is used to spread each aliquot uniformly over the back and each of the two sides of the finger. Each subject rates, on a scale of 1 to 4, the thickness (viscosity), consistency, spreadability and absorbency of the test placebo formulation based on the dispensation and administration procedure. The subject also rates, on a scale of 1 to 4, the feel on the treated area of skin and absence of residue immediately and 5 minutes after application. Also 5 minutes after application the subject rates, on a scale of 1 to 4, the sensory perception and odor of the test formulation. The subject is directed to record any physiological reaction to the test formulation, such as a sense of warming or cooling, any tingling or irritation, and any change in appearance of the skin to which test formulation has been applied.

When more than one test formulation is to be assessed in a single study, the subject is directed to thoroughly wipe the finger used to spread the first test formulation on the first hand and to repeat the procedure with the next test formulation and the opposite hand. Once assessment of test formulation on each hand is complete, the subject is directed to wash their hands thoroughly with soap and water and to wait at least 60 minutes before repeating the procedure with the next pair of test formulations. An esthetics panel is usually conducted using at least five subjects, the ratings from each of whom are analyzed statistically to provide average ratings for each test formulation.

Example 16. Clinical Dose Range-Finding Study for PRM-102 in Treatment of Patients with Raynaud's Phenomenon Secondary to Systemic Sclerosis The effectiveness of topical GTN formulations (PRM-102) for ameliorating symptoms in patients of Raynaud's phenomenon secondary to systemic sclerosis ("SSc-RP") is assessed in a crossover, multi-center randomized, double-blind dose-response study. Efficacy is assessed by measuring changes in finger blood flow and skin temperature in response to a cold challenge. Clinical sites with rheumatologists who routinely treat patients with SSc-RP are selected to identify patients with well-documented SSc-RP to recruit for the study. Physicians at each study site confirm the SSc-RP diagnosis and perform a medical evaluation to ensure that each enrolled patient meets the inclusion and exclusion criteria (Table 14 and Table 15). Clinical staff at each of the selected study sites administer PRM-102 according to a provided protocol. Each site's clinical investigator is responsible for making medical decisions regarding a patient's continued participation in the study.

The study employs three visits. During the first visit (Visit 0), individuals with a clinical diagnosis of SSc-RP as determined by meeting the American College of Rheumatology/European League Against Rheumatism 2013 classification criteria for systemic sclerosis ("SSc") receive and review the study protocol and sign an informed consent document. These individuals are screened for their medical history evaluation and receive a complete physical evaluation. 24 patients meeting the inclusion criteria (Table 14) and not satisfying the exclusion criteria (Table 15) are enrolled in the study. The inclusion and exclusion criteria are intended to ensure that participants have been clinically diagnosed with SSc-RP and are not receiving other therapeutic interventions that may interfere with PRM-102 or skew results of the study. Patients receive a total of 4 different test articles consisting of PRM-102 1.0%, 3.0%, and 8.0% GTN formulations strength formulations or PRM-102 vehicle in a randomized fashion over the course of 2 visits. Two formulations are applied at each visit, one test article to each hand. After application of the test article, patients are subject to cold exposure to induce constriction of blood vessels. Dose-response of PRM-102 is evaluated based on changes in blood flow recovery time determined by infrared thermography ("IRT") scans of the fingers. Treatment visits are separated by a minimum of 48 hours, and the study is concluded within two elapsed weeks. Treatment is discontinued at the request of the patient or the clinical investigator or if there are unacceptable adverse events. Patients receive a complete physical evaluation at the end of the study. Investigators and patients are blinded to the treatment assignments, and a randomization table is provided to the investigator for subject assignment.

All finger blood flow measurements are made using a suitable infrared thermography camera (FLIR ONE Pro iOS from Teledyne FLIR LLC (Wilsonville, OR) attached to a stand with an orthogonal distance of 80 cm from the subject's hands. All images are captured and processed using the commercially available software CTHERM software (Version 2.3, University of Glamorgan).

Baseline IRT images of each hand are taken, and clinic personnel apply one formulation of PRM-102 (1.0%, 3.0%, 8.0%) or vehicle, in a randomized, blinded sequence to the dorsal surface and sides of the four fingers (not including the thumb) of each of the patient's hands. After the application of the test formulations to each hand, IRT images are taken every minute for the first 30 minutes post-application. At 30 minutes post-application, both hands are exposed to a cold challenge in a water bath cooled to 15° C. (±0.5° C.) for 60 seconds. After the cold challenge, IRT images are taken every minute for the first 30 minutes post-cold challenge and then every five minutes for 150 minutes. At three hours post-cold challenge, both hands are exposed to a second cold challenge, and IRT images are taken every minute for 30 minutes after the second cold challenge. This study is designed such that each patient will receive treatment with each formulation of PRM-102 (or vehicle).

For each application, the date and time of application are recorded. IRT images of the regions of interest ("ROI"s) are defined in the baseline and sequential images. The following data are collected by clinic personnel in a blinded fashion:

1. The area under the curve for reperfusion/rewarming in each finger ("AUC") is calculated for each post-challenge images. This value is measured in units of ° C. second.
2. The distal dorsal difference ("DDD"), defined as the difference in temperature between the dorsum of the hand and the finger tips.
3. The maximum blood flow rate/skin temperature after rewarming ("MAX") and the gradient of reperfusion/rewarming in the first five minutes post-cold challenge ("GRAD") are determined.

Data are averaged for all eight fingers of each subject at each treatment. DDD, AUC, MAX, and GRAD are calculated for each subject and each treatment and compared across treatments.

Efficacy evaluations are based on differences in recovery time for blood flow in the fingers, as measured by IRT, differences in skin temperature recovery time measured by IRT, and changes in symptoms of Raynaud's phenomenon in the fingers of the subject.

The independent efficacy indices for this study are:
Primary: Quantitative reduction in blood flow recovery times in the fingers as defined by AUC
Secondary: Quantitative reduction in skin temperature recovery time as defined by DDD, GRAD, and MAX and qualitative reduction in Raynaud's symptoms in fingers as reported using a visual analog scale Any participant who receives at least one dose of PRM-102 is considered evaluable for safety assessment. Safety evaluation involves analyzing the frequency and severity of any adverse experience reported by each participant and those revealed in examination by the clinical investigator. Adverse events include any negative experiences, such as headache, hypotension, lightheadedness, fever, chills, nausea, vomiting, pain or other symptoms that occur during treatment. Participants are required to immediately report any adverse event to the clinical investigator. All minor adverse events are recorded in a Case Report Form ("CRF") and reviewed by the clinical monitor at each monitoring visit. The investigator evaluates the severity of all adverse experiences. The duration of each adverse event and the degree to which it is likely related to the use of PRM-102 is assessed. Any action taken, such as dose modification or implementation of other therapy, is noted. Severe or unexpected adverse events occurring during the study or within four weeks of the participant's last treatment visit are reported within 24 hours of discovery, even should they appear to be unrelated to the use of PRM-102.

Twenty is the number of evaluable subjects targeted. The 24 subject recruitment goal accommodates up to a 15% dropout rate, which is typical for this type of study. Reasons for dropout are summarized and examined to evaluate the possible introduction of bias into the analyses.

The independent efficacy indices for this study are:
Primary: Skin temperature recovery following the clinical induction of constriction of blood vessels upon exposure to cold challenge with the primary endpoint of AUC (area under the curve post-challenge measured with infrared thermography).
Secondary: Skin temperature recovery following the clinical induction of constriction of blood vessels upon exposure to cold challenge with following endpoints (i) GRAD (the gradient of reperfusion/rewarming in the first five minutes post-cold challenge), (ii) DDD (distal-dorsal difference/difference between the fingertip temperature and the temperature of the dorsum), and (iii) MAX (maximum skin temperature after rewarming)

An additional secondary analysis compares the reduction in Raynaud's symptoms in fingers in patients receiving PRM-102 compared to those who receive the control. This qualitative analysis relies on self-reporting by patients. Summary statistics are presented using mean, standard deviations, differences in means, standard errors of difference in means, and 95% confidence intervals for both means and differences in means. AUC, MAX, GRAD, and DDD are evaluated using multi-way ANOVA to compare the differences between the different treatments and to the baseline values in each patient for each sequence administered. Adjustment for relevant covariates is also made in these analyses.

Approximately 24 male or non-pregnant female adults with a clinical diagnosis of RP secondary to Systemic sclerosis of any race are enrolled. This study is conducted during the winter months (December to March), which is the timeframe when most patients experience RP symptoms.

1. 18 years or older.
2. Clinical diagnosis of RP secondary to SSc.
3. At least a 2-phase color change in finger(s) of pallor, cyanosis, and/or reactive hyperemia in response to cold exposure or emotion.
4. Seven years or less disease duration since first non-Raynaud's symptom with SSc.
5. Symmetric symptoms in both hands.
6. Agree to have the test gels applied to their fingers as specified in the protocol.
7. Willing to discontinue current vasodilator therapies for Raynaud's treatment two weeks prior to entry into the study.
8. Agree not to use any other investigational medications or approved therapies to treat RP and its symptoms including other dosage forms of GTN, isosorbide dinitrate, fenoldopam mesylate, milrinone lactate, nifedipine, diltiazem, felodipine, nimodipine, nisoldipine, and verapamil while participating in this study.
9. Female of childbearing potential must agree to use contraception for the duration of the study.
10. Willing and able to comply with the study requirements and give written informed consent for participation in the study.

Table 14. Inclusion Criteria.

1. Currently using any nitrate medication or medications known to interact with GTN, including PDE5 inhibitors such as sildenafil and other treatments for erectile dysfunction.
2. Known allergy to GTN or to common topical gel or lotion ingredients.
3. History of migraine, cluster or vascular headaches, chronic pain with greater intensity than the pain associated with RP or other chronic pain condition of their fingers.
4. History of an unstable medical problem or current medical condition that would contraindicate the administration of PRM-102, interfere with the study evaluations, or interfere with the subject's ability to comply with the study protocol.
5. Cognitive or language difficulties that would impair completion of the pain assessment instruments.
6. Had a myocardial infarction, uncontrolled congestive heart failure, unstable angina, uncontrolled hypotension, or uncontrolled hypertension within the past six months.
7. Participated in a study of any investigational drug within two weeks prior to the first study treatment.
8. Screening laboratory values which are 20% or greater of the upper or lower limit of normal or which are considered to be clinically significant.
9. Systolic blood pressure <85 mmHg.
10. Had a major abdominal, thoracic, or vascular surgery within six months of the first study treatment.
11. Asymmetric Raynaud's symptoms in their hands.
12. Gangrene, digital ulcer infection, requirement of cervical or digital sympathectomy or open lesions or skin conditions in the area where PRM-102 is to be applied.
13. Have used tobacco products of any type and at any level within three months prior to the start of the study and for the duration of the study.
14. Female subjects who are pregnant or breastfeeding.
15. Women of childbearing potential who are unable or unwilling to comply with the contraceptive requirements during the study period.
16. History of poor cooperation, non-compliance with medical treatment or unreliability.
17. Clinically significant disorder that would contraindicate the administration of PRM-102, affect compliance, interfere with study evaluations, or confound the interpretation of study results.

Table 15. Exclusion Criteria.

It is understood that the examples and embodiments described herein are for illustrative purposes only. Various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

We claim:

1. A pharmaceutically-acceptable topical composition comprising at least 4% weight by weight of nitroglycerin, at least 8% oleic acid, 1.425 to 1.575% of an emollient comprising a fatty acid ester of an alpha hydroxy acid, and 2.85 to 3.15% of hydroxypropyl cellulose, and at least 63% by weight of propylene glycol, wherein the composition is free of both water and hydrocarbon, and wherein nitroglycerin is homogeneously distributed throughout said composition.

2. The topical composition of claim 1, wherein said composition is a solution.

3. The topical composition of claim 1, wherein the topical composition comprises at least 5% weight by weight of nitroglycerin.

4. The topical composition of claim 1 wherein said composition further comprises a viscosity-modifying agent selected from hydroxypropyl cellulose, polyoxyethylene sorbitan monooleate, acrylamide/sodium acryloyldimethyl taurate copolymer, or a mixture thereof.

5. The topical composition of claim 1, wherein said fatty acid ester of an alpha hydroxy acid comprises a C12, C13, C14 or C15 alkyl ester of lactic acid, or a mixture thereof.

6. The topical composition of claim 1, further comprising a lubricity-enhancing agent.

7. The topical composition of claim 6, wherein said lubricity-enhancing agent is a silicone.

8. The topical composition of claim 1, further comprising an antioxidant.

9. The topical composition of claim 8, wherein said antioxidant is butylated hydroxytoluene.

10. A pharmaceutically-acceptable topical solution comprising:
 (i) 0.5 to 10% w/w of an active agent selected from nitroglycerin (GTN), pentaerythritol tetranitrate (PETN), isosorbide dinitrate (ISDN), isosorbide mononitrate (ISMN), or a 1,2-dialkoxy-2-propyl nitrate, or a mixture thereof;
 (ii) at least 50% w/w of a diluent selected from alcohols, medium chain triglycerides, a mixture of caprylic triglyceride and capric triglyceride, or propylene glycol;
 (iii) 1 to 15% w/w of a fatty acid;
 (iv) optionally 0.5 to 5% w/w of an emollient;
 (v) 0.1 to 5% w/w a lubricity-enhancing agent;
 (vi) 0.5 to 10% w/w viscosity-modifying agent;
 (vii) optionally 0.25 to 15% w/w of a molecular penetration enhancer (MPE); and
 (viii) optionally an antioxidant.

11. The pharmaceutically-acceptable topical solution of claim 10, wherein:
 (i) the active agent is nitroglycerin (GTN);
 (ii) the diluent is propylene glycol;
 (iii) the fatty acid is selected from oleic acid or isostearic acid;
 (iv) the optional emollient is a fatty acid ester of an alpha hydroxy acid comprising a C12, C13, C14 or C15 alkyl ester of lactic acid, or a mixture of such alkyl esters;
 (v) the lubricity-enhancing agent is selected from a silicone or cyclic siloxane;
 (vi) the viscosity-modifying agent is selected from hydroxypropyl cellulose, polyoxyethylene sorbitan monooleate, acrylamide/sodium acryloyldimethyl taurate copolymer or a mixture thereof;
 (vii) the optional MPE is selected from polyethylene glycol dodecyl ether isopropyl myristate, isopropyl palmitate, dimethyl isosorbide, di(ethylene glycol) ethyl ether or a mixture thereof; and
 (viii) the optional antioxidant is butylated hydroxytoluene.

12. The pharmaceutically-acceptable topical solution of claim 10, wherein the topical solution comprises:
 (i) 0.5 to 10% w/w nitroglycerin;
 (ii) at least 50% w/w propylene glycol;
 (iii) 1 to 15% w/w oleic acid or isostearic acid;
 (iv) optionally 0.5 to 5% w/w a fatty acid ester of an alpha hydroxy acid;
 (v) 0.1 to 5% w/w cyclomethicone;
 (vi) 0.5 to 10% w/w hydroxypropyl cellulose or acrylamide/sodium acryloyldimethyl taurate copolymer;
 (vii) optionally 0.25 to 15% w/w polyethylene glycol dodecyl ether, isopropyl myristate, dimethyl isosorbide, di(ethylene glycol) ethyl ether or a mixture thereof; and
 (viii) optionally 0.05-0.8% butylated hydroxytoluene.

13. The topical solution according to claim 10, wherein the topical solution is manufactured by: (i) providing appropriate amounts of all excipients other than diluent and viscosity-modifying agent into a vessel, (ii) providing the appropriate amount of active agent combined, where required by the composition, with diluent, into said vessel (iii) agitating the mixture in said vessel until homogeneous, (iv) providing into said vessel the appropriate quantity of viscosity-modifying agent, and (v) mixing the combination thoroughly.

14. A method for treating a condition in a subject in which peripheral blood flow is compromised comprising topical administration of the topical solution of claim 10.

15. The method of claim 14 wherein said condition is a chronic tendinopathy, mastectomy skin flap necrosis, autonomic dysreflexia associated with spinal cord injury, intraoperative microsurgical vasospasm, chondrodermatitis nodularis helicis, chronic anal fissure, introital dyspareunia, vulvar pain associated with vulvodynia, or Raynaud's phenomenon.

16. The method of claim 14 wherein said condition is selected from the group consisting of peripheral artery disease, peripheral vascular disease, diabetic neuropathy, tendinopathy, erectile dysfunction, alopecia, male pattern baldness and female pattern baldness.

17. The method of claim 14 wherein said condition is primary Raynaud's phenomenon or secondary Raynaud's phenomenon associated with one or more of: systemic sclerosis, CREST syndrome, systemic lupus erythematosus, rheumatoid disease, rheumatoid arthritis, Sjogren's syndrome, or polymyositis.

* * * * *